US012329472B2

(12) United States Patent
Waterbury et al.

(10) Patent No.: US 12,329,472 B2
(45) Date of Patent: Jun. 17, 2025

(54) CABLE LENGTH CONSERVING MEDICAL INSTRUMENT

(71) Applicant: Intuitive Surgical Operations, Inc., Sunnyvale, CA (US)

(72) Inventors: Andrew C. Waterbury, Sunnyvale, CA (US); John Ryan Steger, Sunnyvale, CA (US); Zhou Ye, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 717 days.

(21) Appl. No.: 17/561,294

(22) Filed: Dec. 23, 2021

(65) Prior Publication Data
US 2022/0192764 A1  Jun. 23, 2022

Related U.S. Application Data

(63) Continuation of application No. 16/462,114, filed as application No. PCT/US2017/062258 on Nov. 17, 2017, now Pat. No. 11,241,290.
(Continued)

(51) Int. Cl.
*A61B 34/30* (2016.01)
*A61B 17/29* (2006.01)
(Continued)

(52) U.S. Cl.
CPC .............. *A61B 34/30* (2016.02); *A61B 34/71* (2016.02); *A61B 2017/00323* (2013.01);
(Continued)

(58) Field of Classification Search
CPC ........... A61B 2017/00323; A61B 2017/00477; A61B 2017/2932; A61B 2034/305; A61B 2034/715; A61B 34/30; A61B 34/71
See application file for complete search history.

(56) References Cited

U.S. PATENT DOCUMENTS 2,091,317 A  8/1937  Hill
2,537,339 A  1/1951  Meyer et al.
(Continued)

FOREIGN PATENT DOCUMENTS

CN  104116547 A  10/2014
CN  104799891 A  7/2015
(Continued)

OTHER PUBLICATIONS

Extended European Search Report for Application No. EP17872579.2 mailed on May 29, 2020, 8 pages.
(Continued)

*Primary Examiner* — Majid Jamialahmadi

(57) ABSTRACT

An apparatus includes a wrist, an end effector, a cable pair, and a transmission. A proximal wrist portion is coupled to a distal end portion of a shaft. Actuation of the wrist moves a distal wrist portion relative to the proximal wrist portion. The end effector is coupled to the distal wrist portion, and can be actuated to move relative to the wrist. The transmission is coupled to a proximal end portion of the shaft, and can move an end of the cable pair to actuate the end effector. The end of the cable pair is routed through a transmission cable path within the transmission. The transmission includes an adjustment mechanism having an input portion that receives a force exerted by the end of the cable pair. The adjustment mechanism is configured to change a length of the transmission cable path in response to a change in the force.

14 Claims, 14 Drawing Sheets

Related U.S. Application Data

(60) Provisional application No. 62/424,744, filed on Nov. 21, 2016.

(51) Int. Cl.
*A61B 34/00* (2016.01)
*A61B 17/00* (2006.01)
*B25J 9/10* (2006.01)
*B25J 15/00* (2006.01)
*B25J 17/02* (2006.01)

(52) U.S. Cl.
CPC . *A61B 2017/2932* (2013.01); *A61B 2034/305* (2016.02); *A61B 2034/715* (2016.02); *B25J 9/104* (2013.01); *B25J 15/00* (2013.01); *B25J 17/02* (2013.01)

(56) References Cited

U.S. PATENT DOCUMENTS

| | | |
|---|---|---|
| 4,341,144 A | 7/1982 | Milne |
| 4,763,531 A | 8/1988 | Dietrich et al. |
| 4,787,256 A | 11/1988 | Cherbuy et al. |
| 4,799,752 A | 1/1989 | Carome |
| 4,869,113 A | 9/1989 | Sarrazin |
| 5,792,135 A | 8/1998 | Madhani et al. |
| 5,807,377 A * | 9/1998 | Madhani .............. A61B 34/77 606/1 |
| 5,876,325 A | 3/1999 | Mizuno et al. |
| 6,007,550 A | 12/1999 | Wang et al. |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,676,684 B1 | 1/2004 | Morley et al. |
| 6,817,974 B2 | 11/2004 | Cooper et al. |
| 6,994,708 B2 | 2/2006 | Manzo |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,371,210 B2 | 5/2008 | Brock et al. |
| 7,582,055 B2 | 9/2009 | Komiya et al. |
| 7,608,083 B2 | 10/2009 | Lee et al. |
| 7,666,191 B2 | 2/2010 | Orban, III et al. |
| 7,935,130 B2 | 5/2011 | Williams |
| 8,142,421 B2 | 3/2012 | Cooper et al. |
| 8,224,484 B2 | 7/2012 | Swarup et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,597,280 B2 | 12/2013 | Cooper et al. |
| 8,603,077 B2 | 12/2013 | Cooper et al. |
| 8,771,270 B2 | 7/2014 | Burbank |
| 8,800,838 B2 | 8/2014 | Shelton, IV |
| 8,808,166 B2 | 8/2014 | Hosaka |
| 8,911,471 B2 | 12/2014 | Spivey et al. |
| 8,939,963 B2 | 1/2015 | Rogers et al. |
| 8,992,565 B2 | 3/2015 | Brisson et al. |
| 9,028,494 B2 | 5/2015 | Shelton, IV et al. |
| 9,078,684 B2 | 7/2015 | Williams |
| 9,198,729 B2 | 12/2015 | Rogers |
| 9,204,923 B2 | 12/2015 | Manzo et al. |
| 9,232,979 B2 | 1/2016 | Parihar et al. |
| 9,259,274 B2 | 2/2016 | Prisco |
| 9,259,275 B2 | 2/2016 | Burbank |
| 9,572,616 B2 | 2/2017 | Vaughn |
| 9,839,439 B2 | 12/2017 | Cooper et al. |
| 9,931,106 B2 | 4/2018 | Au et al. |
| 10,130,366 B2 | 11/2018 | Shelton, IV et al. |
| 10,219,874 B2 | 3/2019 | Yu et al. |
| 10,299,873 B2 | 5/2019 | Hares et al. |
| 10,314,583 B2 | 6/2019 | Smith et al. |
| 10,357,321 B2 | 7/2019 | Donlon et al. |
| 10,470,830 B2 | 11/2019 | Hill et al. |
| 10,478,256 B2 | 11/2019 | Shelton, IV et al. |
| 10,550,918 B2 | 2/2020 | Cooper et al. |
| 10,595,948 B2 | 3/2020 | Solomon et al. |
| 10,595,949 B2 | 3/2020 | Donlon et al. |
| 10,682,141 B2 | 6/2020 | Moore et al. |
| 10,779,898 B2 | 9/2020 | Hill et al. |
| 10,806,530 B2 | 10/2020 | Liao et al. |
| 10,813,706 B2 | 10/2020 | Chaplin et al. |
| 10,932,868 B2 | 3/2021 | Solomon et al. |
| 11,013,566 B2 | 5/2021 | Diel et al. |
| 11,129,686 B2 | 9/2021 | Chaplin et al. |
| 11,241,290 B2 | 2/2022 | Waterbury et al. |
| 11,248,686 B2 | 2/2022 | Cooper et al. |
| 11,304,770 B2 | 4/2022 | Crews et al. |
| 11,517,397 B2 | 12/2022 | Lambrecht et al. |
| 2002/0111635 A1 | 8/2002 | Jensen et al. |
| 2005/0119527 A1 | 6/2005 | Banik et al. |
| 2006/0074415 A1 | 4/2006 | Scott et al. |
| 2006/0276775 A1 | 12/2006 | Rosenberg et al. |
| 2007/0043338 A1 | 2/2007 | Moll et al. |
| 2007/0119274 A1 | 5/2007 | Devengenzo et al. |
| 2007/0137371 A1 | 6/2007 | Devengenzo et al. |
| 2007/0208375 A1 | 9/2007 | Nishizawa et al. |
| 2007/0232858 A1 | 10/2007 | MacNamara et al. |
| 2008/0009838 A1 | 1/2008 | Schena et al. |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0088774 A1 | 4/2009 | Swarup et al. |
| 2009/0198272 A1 | 8/2009 | Kerver et al. |
| 2010/0011900 A1 | 1/2010 | Burbank et al. |
| 2010/0175701 A1 | 7/2010 | Reis et al. |
| 2010/0198218 A1 | 8/2010 | Manzo |
| 2010/0198253 A1 | 8/2010 | Jinno et al. |
| 2010/0318101 A1 | 12/2010 | Choi et al. |
| 2011/0015650 A1 | 1/2011 | Choi et al. |
| 2011/0071543 A1 | 3/2011 | Prisco et al. |
| 2011/0118754 A1 | 5/2011 | Dachs, II et al. |
| 2011/0184241 A1 | 7/2011 | Zubiate et al. |
| 2011/0218551 A1 | 9/2011 | Devengenzo et al. |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0046522 A1 | 2/2012 | Naito |
| 2012/0109186 A1 | 5/2012 | Parrott et al. |
| 2012/0123441 A1 | 5/2012 | Au et al. |
| 2012/0150192 A1 | 6/2012 | Dachs et al. |
| 2012/0289974 A1 | 11/2012 | Rogers et al. |
| 2012/0292367 A1 | 11/2012 | Morgan et al. |
| 2012/0298719 A1 | 11/2012 | Shelton, IV et al. |
| 2012/0330287 A1 | 12/2012 | Yim |
| 2013/0046318 A1 | 2/2013 | Radgowski et al. |
| 2013/0144395 A1 | 6/2013 | Stefanchik et al. |
| 2013/0304084 A1 | 11/2013 | Beira et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0114327 A1 | 4/2014 | Boudreaux et al. |
| 2014/0257333 A1 | 9/2014 | Blumenkranz |
| 2014/0309625 A1 | 10/2014 | Okamoto et al. |
| 2015/0005786 A1 | 1/2015 | Burbank |
| 2015/0150635 A1 | 6/2015 | Kilroy et al. |
| 2015/0150636 A1 | 6/2015 | Hagn et al. |
| 2015/0157355 A1 | 6/2015 | Price et al. |
| 2016/0184034 A1 | 6/2016 | Holop et al. |
| 2016/0361049 A1 | 12/2016 | Dachs, II et al. |
| 2017/0007345 A1 | 1/2017 | Smith et al. |
| 2017/0165017 A1 | 6/2017 | Chaplin et al. |
| 2018/0055583 A1 | 3/2018 | Schuh et al. |
| 2018/0080533 A1 | 3/2018 | Awtar |
| 2018/0116743 A1 | 5/2018 | Burbank et al. |
| 2018/0126504 A1 | 5/2018 | Shelton, IV et al. |
| 2019/0038282 A1 | 2/2019 | Shelton, IV et al. |
| 2019/0117325 A1 | 4/2019 | Kishi |
| 2019/0125468 A1 | 5/2019 | Adams |
| 2019/0159846 A1 | 5/2019 | Yates et al. |

(56) References Cited

U.S. PATENT DOCUMENTS

| | | |
|---|---|---|
| 2019/0223960 A1 | 7/2019 | Chaplin et al. |
| 2019/0231374 A1 | 8/2019 | Kimura et al. |
| 2019/0231464 A1 | 8/2019 | Wixey et al. |
| 2019/0307522 A1 | 10/2019 | Lambrecht et al. |
| 2019/0328467 A1 | 10/2019 | Waterbury et al. |
| 2020/0197117 A1 | 6/2020 | Donlon et al. |
| 2021/0196413 A1 | 7/2021 | Inoue |
| 2021/0372508 A1 | 12/2021 | Abbott |
| 2022/0000572 A1 | 1/2022 | Ragosta et al. |
| 2022/0128133 A1 | 4/2022 | Cooper et al. |
| 2023/0079266 A1 | 3/2023 | Wixey et al. |
| 2023/0119001 A1 | 4/2023 | Abbott |
| 2024/0156551 A1 | 5/2024 | Lambrecht et al. |

FOREIGN PATENT DOCUMENTS

| | | |
|---|---|---|
| CN | 105163679 A | 12/2015 |
| EP | 2362285 A2 | 8/2011 |
| EP | 2548529 A1 | 1/2013 |
| EP | 2627278 A1 | 8/2013 |
| EP | 2783643 A1 | 10/2014 |
| EP | 3195993 A1 | 7/2017 |
| JP | H06114000 A | 4/1994 |
| JP | H10249777 A | 9/1998 |
| JP | 2002200091 A | 7/2002 |
| JP | 2004337994 A | 12/2004 |
| JP | 2005288590 A | 10/2005 |
| WO | WO-9729690 A1 | 8/1997 |
| WO | WO-0030557 A1 | 6/2000 |
| WO | WO-2010009224 A1 | 1/2010 |
| WO | WO-2010081050 A1 | 7/2010 |
| WO | WO-2011060046 A2 | 5/2011 |
| WO | WO-2012064528 A1 | 5/2012 |
| WO | WO-2012068156 A2 | 5/2012 |
| WO | WO-2015142290 A1 | 9/2015 |
| WO | WO-2016161449 A1 | 10/2016 |
| WO | WO-2016172299 A1 | 10/2016 |
| WO | WO-2016189284 A1 | 12/2016 |
| WO | WO-2017064303 A1 | 4/2017 |
| WO | WO-2017188851 A1 | 11/2017 |
| WO | WO-2018013313 A1 | 1/2018 |
| WO | WO-2018049217 A1 | 3/2018 |
| WO | WO-2018069679 A1 | 4/2018 |
| WO | WO-2020102776 A1 | 5/2020 |
| WO | WO-2020102780 A1 | 5/2020 |
| WO | WO-2020252184 A1 | 12/2020 |
| WO | WO-2023055684 A2 | 4/2023 |

OTHER PUBLICATIONS

International Search Report and Written Opinion for Application No. PCT/US2017/062258, mailed on Mar. 16, 2018, 13 pages.

Office Action for CN Application No. 201780083152.4, mailed Sep. 16, 2021, 24 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for EP Application No. 17872579.2, mailed Nov. 20, 2023, 04 pages.

* cited by examiner

CABLE LENGTH CONSERVING MEDICAL INSTRUMENT

CROSS-REFERENCE TO RELATED APPLICATIONS

This application is a continuation of U.S. patent application Ser. No. 16/462,114 (filed May 17, 2019)(entitled "Cable Length Conserving Medical Instrument"), which is a U.S. national stage filing under 35 U.S.C. § 371 of International Application No. PCT/US2017/062258 (filed Nov. 17, 2017)(entitled "Cable Length Conserving Medical Instrument"), which claims benefit of priority to U.S. Provisional Patent Application No. 62/424,744 (filed Nov. 21, 2016) (entitled "Cable Length Conserving Medical Instrument"), each of which is incorporated herein by reference in its entirety.

BACKGROUND

The embodiments described herein relate to mechanisms for conserving cable length, more specifically to medical devices, and still more specifically to endoscopic tools. More particularly, the embodiments described herein relate to devices that include a mechanism for conserving the cable length during a range of motion of a wrist joint.

Many known medical instruments for minimally invasive procedures may employ one or more joints or wrists along an elongated shaft sometimes referred to herein as the main shaft of the medical instrument. Typically, a wrist provides multiple degrees of freedom of movement, and a wrist at or near the distal end of the main shaft may be attached to or may incorporate a distal tool such as a biopsy needle, a scalpel, forceps, scissors, or a cautery tool. Such known wrists are often operated via cables that extend through the interior of the main shaft of the instrument and connect to a drive system in a transmission or actuator (also referred to as a backend). The backend is generally at the proximal end of the medical instrument and may be configured to engage or interface with a robot that mechanically powers the backend to move the cables, thereby operating the wrist. For robotic or teleoperated systems, the backend mechanism is motor driven and can be operably coupled to a processing system to provide a user interface for a user to control the instrument. During a minimally invasive procedure, medical personnel may operate the system to insert the distal portion of a medical instrument through a small incision, a cannula, or a natural lumen until the distal tip of the medical instrument is at a work site in a patient, and the medical personnel may then operate the robot to drive the cables and control the wrist as needed to move the distal tool and perform a clinical function at the work site.

Known medical instruments define one or more cable paths through which the cables are routed from the backend, through the instrument shaft, and to the wrist. Because known wrists can provide for multiple degrees of freedom, the cable paths (and therefore the length of the cables through the cable paths) can change when the medical instrument is in use. For example, when some known wrists rotate about a pitch axis, the cable path length for cables routed on a first side of the pitch axis increases while the cable path length for cables routed on a second (or opposite) side of the pitch axis decreases. The increased cable path length tends to stretch or increase tension in the cables on the first side of the pitch axis, and decreased cable path length allows the cables on the second side of the pitch axis to go slack or operate under reduced tension in the cables. In general, it is desirable to maintain the tension in cables within a suitable range to prevent slack cables from derailing and to prevent tight cables from deforming or damaging other components. Thus, some known medical instruments include cable paths within the wrist that are routed to minimize the change in the cable path length during actuation. This is sometimes referred to herein as cable length conservation.

For example, FIGS. 1A and 1B show top and side schematic views of a known medical instrument 100. The medical instrument 100 includes a wrist 130 that is at a distal end of a main shaft 120 of the medical instrument 100 and is actuated via a backend 110. Wrist 130 includes actuated mechanisms 140 and 150 that together are capable of multiple degrees of freedom of movement. In the illustrated configuration, actuated mechanism 140 is a joint that may be actuated to provide a degree of freedom corresponding to pitch motion. The actuated mechanism 140 includes a link 142 coupled to main shaft 120 and a link 144 coupled to the actuated mechanism 150. A pair of cables 126a and 126b coupled to actuated mechanism 140 extend through main shaft 120 and couple to a drive mechanism (not shown) in the backend 110. Thus, the drive mechanism can pull either cable 126a or 126b to rotate link 144 (and more distal portions of medical instrument 100) relative to link 142 as shown in FIG. 1C.

The actuated mechanism 150 (also referred to as an end effector) includes jaws 152 and 154, which may act as another wrist degree of freedom (e.g., yaw motion) when they rotate together and as a surgical tool such as forceps or scissors when they rotate in opposite directions. Jaws 152 and 154 are mounted on a pivot 156, which may be offset from and perpendicular to rotation axis 146 (i.e., the pitch axis) of joint 140. A pair of cables 122a and 122b couple to jaw 152 and extend through joint 140 and main shaft 120 to a drive mechanism 112 in backend 110, and drive mechanism 112 can pull either cable 122a or 122b to rotate jaw 152 about pivot 156. Similarly, another pair of actuation cables 124 couple to jaw 154 and extend through actuated mechanism 140 and main shaft 120 to backend 110, and another drive mechanism (not shown) in backend 110 can pull either cable 124 to rotate jaw 154 about the shared pivot 156. FIG. 1B illustrates how drive mechanism 112 for cables 122a and 122b may include a capstan 112 from which cables 122a and 122b extend. In use, an actuator, such as a motor in the control robot, can rotate capstan 112 to reel in a length of cable 122b or 122a and simultaneously pay out the same length of cable 122a or 122b, resulting in rotation of jaw 152. Another motor and capstan (not shown) can drive cables 124 to rotate jaw 154.

As shown in FIG. 1A, cables 122 and 124 have crossing paths and are routed through the rotation axis 146 of joint 140 so that rotation of joint 140 does not change the path length of cables 122 and 124 between backend mechanism 110 and actuated mechanism 150. In this manner, the cable paths within the joint 140 maintain a substantially constant length of cables 122 and 124 between backend 110 and actuated mechanism 150, even when the joint 140 is moved about the pitch axis 146 (see e.g., FIG. 1C). Thus, this known joint assembly can be considered as a cable length-conserving device.

In certain situations, however, defining cable length-conserving paths within a wrist joint is not practical. For example, medical instruments that include many functional elements or other components routed to an end effector (e.g., wires) may not accommodate cable length-conserving paths. Similarly, medical instruments having joints with a small cross-sectional area or diameter may not have sufficient space to accommodate routing of multiple cables for cable length conservation. In particular, as wrist architectures for medical instruments are scaled down to diameters of 5 mm or less, space limitations make joints with cable length-conserving cable paths challenging to implement, while still using cables having sufficient strength for the desired medical capabilities.

Thus, a need exists for improved mechanisms to accommodate different cable path lengths between a medical instrument's distal and proximal ends that result from a distal component's range of motion.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a cable length conserving medical instrument includes a path-length adjusting drive mechanism, which may be located in the backend of a medical instrument, and may eliminate the need for distal cable pathways routings to be inherently length conserving. The drive mechanism may particularly include mechanisms that autonomously change backend cable routings to compensate for distal path length changes, so that the medical instrument, as a whole, provides path-length conservation. As a result, the combination of drive mechanisms and wrists allow simple capstan actuation, and an external control system does not need to actively monitor or adjust cable length tension. In some implementations, a tension change induced by a lack of length conservation in one portion of the instrument actuates a route-altering mechanism to compensate for the remote lack of length conservation, for example, so that the path lengths for one pair of cables increases in response to tension decreasing the path lengths of another pair of cables.

In some embodiments, an apparatus includes a wrist assembly, an end effector, a cable pair, and a transmission. The wrist assembly has a proximal wrist portion and a distal wrist portion. The proximal wrist portion is coupled to a distal end portion of a shaft. Actuation of the wrist assembly produces movement of the distal wrist portion relative to the proximal wrist portion. The wrist assembly defines a wrist cable path having a length that changes when the distal wrist portion moves relative to the proximal wrist portion. The end effector is coupled to the distal wrist portion. Actuation of the end effector produces movement of the end effector relative to the distal wrist portion. The cable pair is routed through the wrist cable path, and a first end of the cable pair is coupled to the end effector. The transmission is coupled to a proximal end portion of the shaft, and can move a second end of the cable pair to actuate the end effector. The second end of the cable pair is routed through a transmission cable path within the transmission. The transmission includes an adjustment mechanism configured to change a length of the transmission cable path in response to a change in the length of the wrist cable path.

In some embodiments, an apparatus includes a wrist assembly, an end effector, a cable pair, and a transmission. The wrist assembly has a proximal wrist portion and a distal wrist portion. The proximal wrist portion is coupled to a distal end portion of a shaft. Actuation of the wrist assembly produces movement of the distal wrist portion relative to the proximal wrist portion. The end effector is coupled to the distal wrist portion. Actuation of the end effector produces movement of the end effector relative to the distal wrist portion. The cable pair has a first end and a second end, the first end being coupled to the end effector. The transmission is coupled to a proximal end portion of the shaft, and can move a second end of the cable pair to actuate the end effector. The second end of the cable pair is routed through a transmission cable path within the transmission. The transmission includes an adjustment mechanism having an input portion that receives a force exerted by the second end of the cable pair. The adjustment mechanism is configured to change a length of the transmission cable path in response to a change in the force exerted by the second end of the cable pair.

DETAILED DESCRIPTION

Figure 1A:
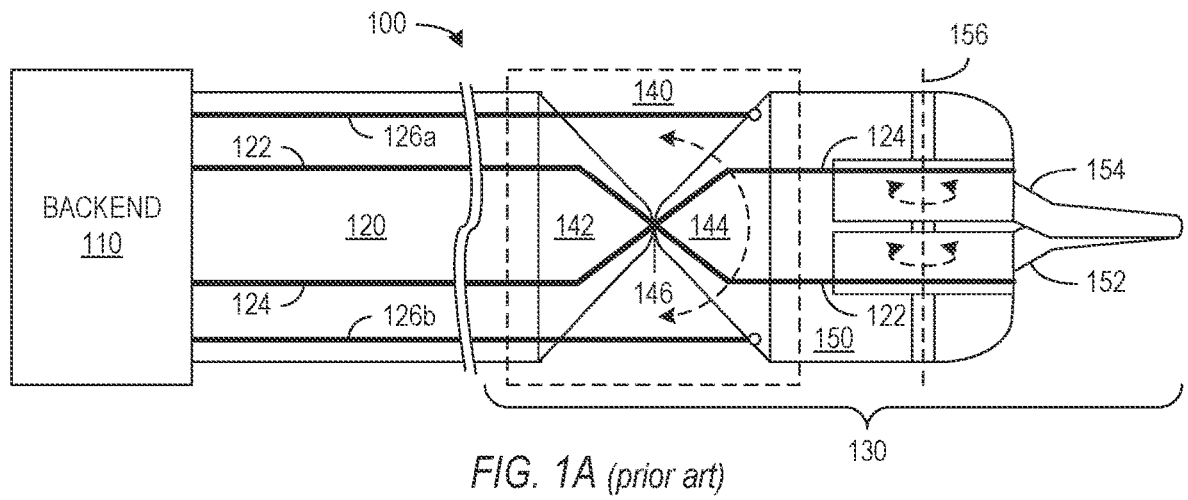
FIGS. 1A and 1B show schematic side and top views of a prior art medical instrument employing cable length conserving routings.
Figure 1B:
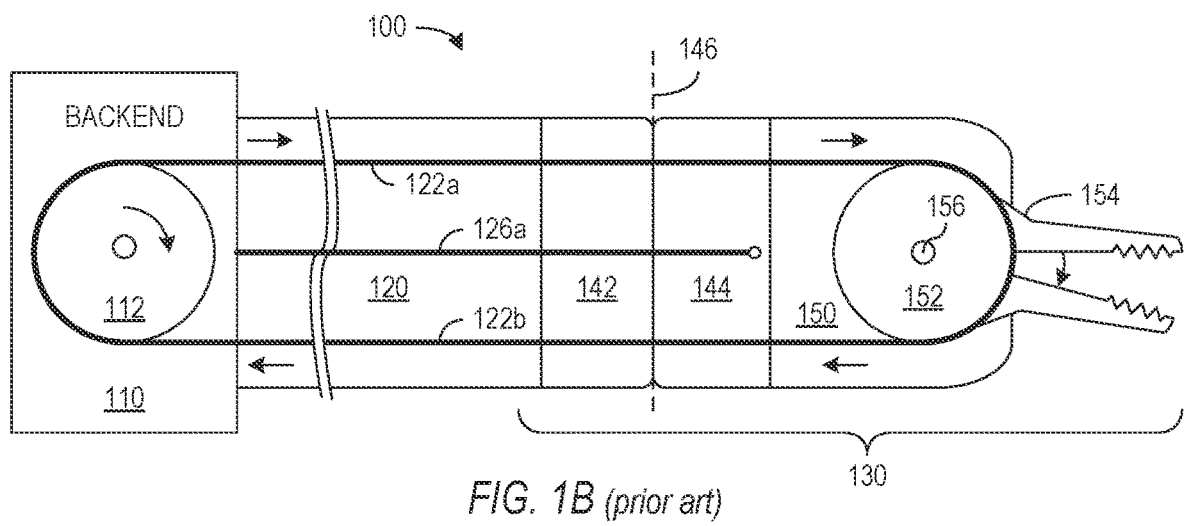
Figure 1C:
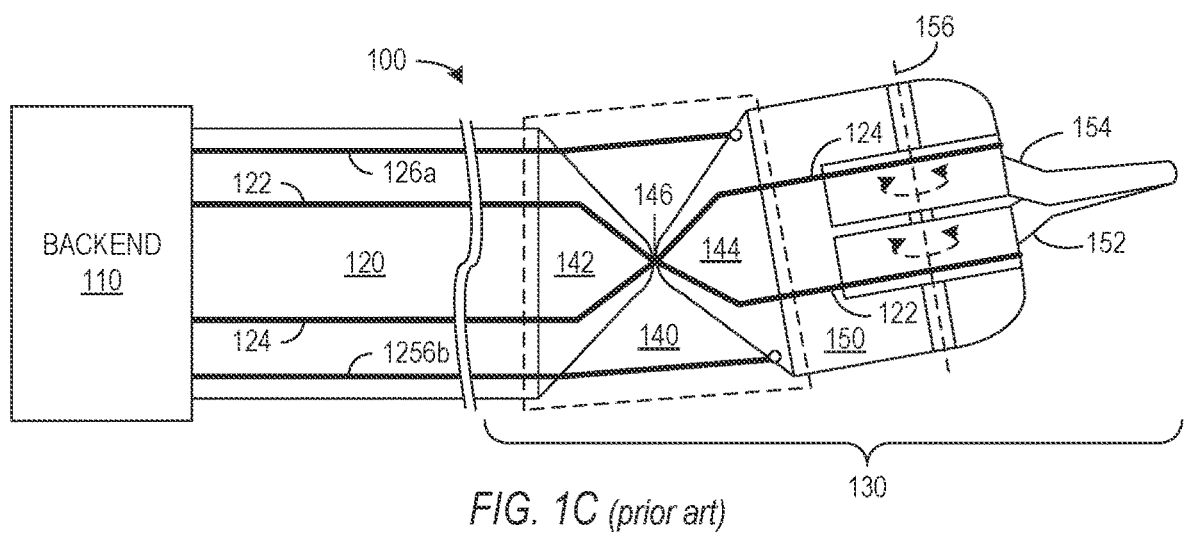
FIG. 1C shows a schematic side view of the medical instrument of FIG. 1A when a distal portion of the wrist is rotated about a pitch axis.

The embodiments described herein can advantageously conserve cable length for both pitch and yaw motions of a wrist assembly by permitting cable path length changes in the wrist and autonomously applying compensating cable path length changes in the instrument transmission (e.g., located at a proximal end of an instrument). This arrangement can facilitate improved instrument performance in reduced size instruments. In such applications, the size of the wrist may not allow sufficient room for inherently length conserving paths for all cables traversing the wrist, thus, the embodiments described herein include a route-altering mechanism to change cable routing in the transmission (or backend) to at least approximately conserve the overall length of cables from the transmission actuators (e.g., drive capstans) to actuated mechanisms (e.g., an end effector). For example, a medical instrument lacking room for the yaw actuation cables to cross through the pitch axis of a wrist may include a drive mechanism of the types shown and described herein that compensates for a lack of cable length conservation in the wrist.

In some embodiments, a wrist assembly may route cables (e.g., yaw actuation cables that actuate an end effector) past a joint and at an offset relative to a rotation axis of the joint. As a result, when the wrist assembly rotates about the joint (e.g., pitch rotation), the path lengths of cables on one side of the rotation axis increase, which tends to stretch or increase tension in some cables, and the path lengths of cables on the opposite side of the rotation axis decrease, which allows some cables to go slack or reduces tension in the cables. In such embodiments, the adjustment mechanisms described herein can maintain the tension in the cables within a suitable range during rotation by adjusting a tension or cable path length in the proximal end portion of the instrument. This prevents slack cables from derailing and prevents tight cables from deforming or damaging other components.

In some embodiments, an apparatus includes a wrist assembly, an end effector, a cable pair, and a transmission. The wrist assembly has a proximal wrist portion and a distal wrist portion. The proximal wrist portion is coupled to a distal end portion of a shaft. Actuation of the wrist assembly produces movement of the distal wrist portion relative to the proximal wrist portion. The wrist assembly defines a wrist cable path having a length that changes when the distal wrist portion moves relative to the proximal wrist portion. The end effector is coupled to the distal wrist portion. Actuation of the end effector produces movement of the end effector relative to the distal wrist portion. The cable pair is routed through the wrist cable path, and a first end of the cable pair is coupled to the end effector. The transmission is coupled to a proximal end portion of the shaft, and can move a second end of the cable pair to actuate the end effector. The second end of the cable pair is routed through a transmission cable path within the transmission. The transmission includes an adjustment mechanism configured to change a length of the transmission cable path in response to a change in the length of the wrist cable path.

In some embodiments, an apparatus includes a wrist assembly, an end effector, a cable pair, and a transmission. The wrist assembly has a proximal wrist portion and a distal wrist portion. The proximal wrist portion is coupled to a distal end portion of a shaft. Actuation of the wrist assembly produces movement of the distal wrist portion relative to the proximal wrist portion. The end effector is coupled to the distal wrist portion. Actuation of the end effector produces movement of the end effector relative to the distal wrist portion. The cable pair has a first end and a second end, the first end being coupled to the end effector. The transmission is coupled to a proximal end portion of the shaft, and can move a second end of the cable pair to actuate the end effector. The second end of the cable pair is routed through a transmission cable path within the transmission. The transmission includes an adjustment mechanism having an input portion that receives a force exerted by the second end of the cable pair. The adjustment mechanism is configured to change a length of the transmission cable path in response to a change in the force exerted by the second end of the cable pair.

In some embodiments, an apparatus includes a wrist assembly, an end effector, a cable pair, a transmission, and an adjustment means. The wrist assembly has a proximal wrist portion and a distal wrist portion. The proximal wrist portion is coupled to a distal end portion of a shaft. Actuation of the wrist assembly produces movement of the distal wrist portion relative to the proximal wrist portion. The wrist assembly defines a wrist cable path having a length that changes when the distal wrist portion moves relative to the proximal wrist portion. The end effector is coupled to the distal wrist portion. Actuation of the end effector produces movement of the end effector relative to the distal wrist portion. The cable pair is routed through the wrist cable path and has a first end coupled to the end effector. The transmission is coupled to a proximal end portion of the shaft, and includes an actuator that moves a second end of the cable pair to actuate the end effector. The second end of the cable pair is routed through a transmission cable path within the transmission. The adjustment means is configured to change a length of the transmission cable path in response to a change in the length of the wrist cable path.

In some embodiments, a medical instrument includes a drive mechanism, a shaft extending from the drive mechanism, and an actuated mechanism on the shaft. A pair of cables has a routing in the actuated mechanism and through the shaft to the drive mechanism, and an actuation of a degree of freedom of the actuated mechanism causes a change in a path length of the pair of cables outside the drive mechanism. The drive mechanism includes a route-altering mechanism that engages the pair of cables, and during the actuation, the route-altering mechanism autonomously changes a path length of the first pair of cables in the drive mechanism to compensate for the change in the path length of the first pair of cables in the actuated mechanism.

In some embodiments, a medical instrument includes a transmission, a shaft extending from the transmission, and a drive mechanism in the transmission. A first pair of cables extends from the transmission, through the main shaft, to an actuated mechanism and is coupled to actuate a first degree of freedom of the actuated mechanism. A second pair of cables extends from the transmission, through the main shaft, and to the actuated mechanism. The second pair of cables is coupled to actuate a second degree of freedom of the actuated mechanism. The drive mechanism is coupled to the first and second pairs of cables and includes a route-altering mechanism that alters routings of the first and second pair of cables in response to a tension change induced by a lack of length conservation in paths of the first and second pairs of cables through the shaft to actuate the mechanism.

In some embodiments, an apparatus includes a chassis, a cable pair, an actuator, and an adjustment mechanism. The chassis is coupled to a proximal end portion of a shaft. A distal end portion of the shaft is configured to be coupled to a wrist assembly. The cable pair is routed through the shaft and has a first end and a second end. The first end of the cable pair is configured to be coupled to the wrist assembly. The second end of the cable pair is routed through a transmission cable path within the chassis. The actuator is within the chassis, and is configured to move the second end of the cable pair. The adjustment mechanism has an input portion that receives a force exerted by the second end of the cable pair. The adjustment mechanism is configured to change a length of the transmission cable path in response to a change in the force exerted by the second end of the cable pair.

Methods of manipulating an instrument are also described herein. In some embodiments, a method includes actuating a wrist assembly of an instrument to cause a distal wrist portion to move relative to a proximal wrist portion from a first position to a second position. The proximal wrist portion is coupled to a distal end portion of a shaft. The distal wrist portion is coupled to an end effector. A cable pair is routed through a wrist cable path such that a first end of the cable pair is coupled to the end effector and a second end of the cable pair is coupled to an actuator within a transmission (also referred to as a backend). The transmission is coupled to a proximal end portion of the shaft. A length of the wrist cable path changes when the distal wrist portion moves from the first position to the second position. A length of a transmission cable path through which the second end of the cable pair is routed is changed in response to the change in the length of the wrist cable path. The second end of the cable pair is moved, via an actuator within the transmission, to actuate the end effector.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used in this specification, the word "distal" refers to direction towards a work site, and the word "proximal" refers to a direction away from the work site. Thus, for example, the end of an instrument that is closest to the target tissue would be the distal end of the tool, and the end opposite the distal end (i.e., the end manipulated by the user) would be the proximal end of the instrument.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a surgical system, such as, for example, the da Vinci® Surgical System, commercialized by Intuitive Surgical, Inc. of Sunnyvale, California. Examples of such surgical systems are the da Vinci® Xi™ Surgical System (Model IS4000) and the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

Figure 2A:
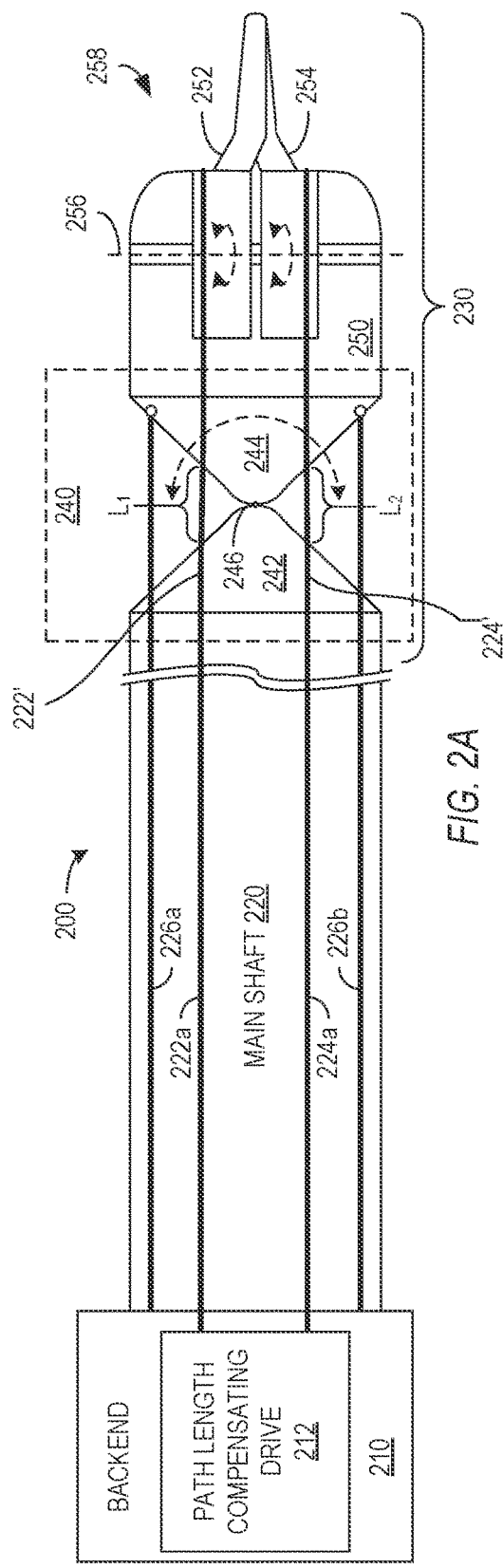
FIGS. 2A and 2B show side views of a medical instrument including a drive mechanism that compensates for distal cable routing that does not conserve cable length, according to an embodiment.
Figure 2B:
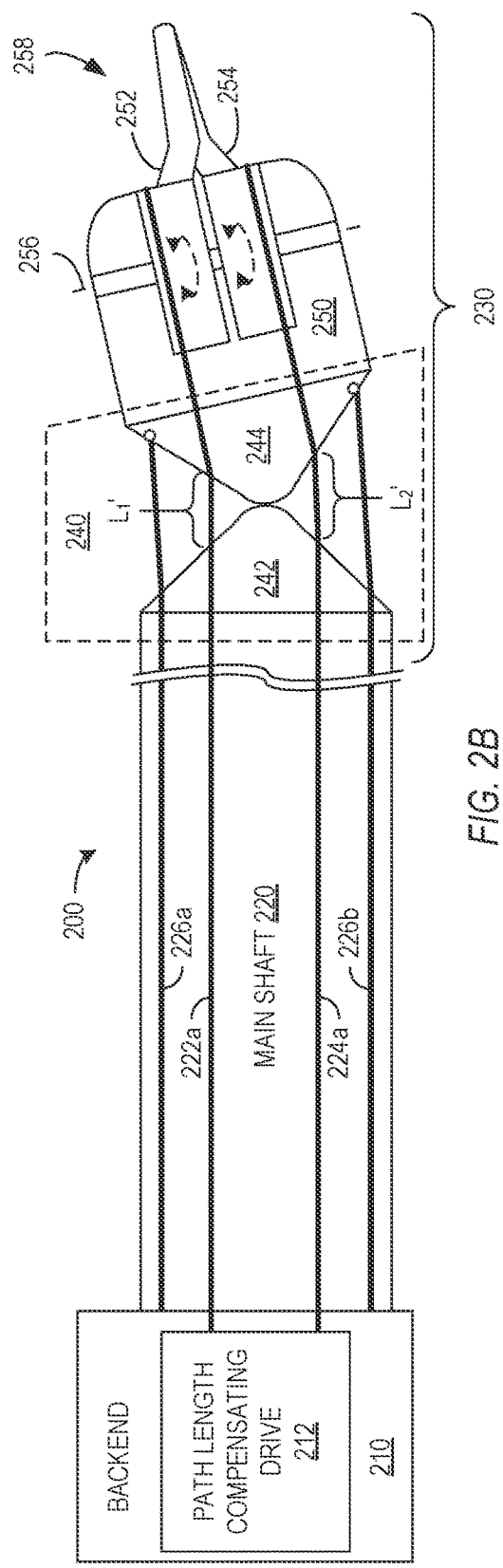

FIGS. 2A and 2B illustrate schematic side views of a medical instrument 200, which may be used for minimally invasive medical procedures. Medical instrument 200 includes a wrist 230 including a pitch joint 240 through which a first pair of actuation cables 222a and 222b and a second pair of actuation cables 224a and 224b extend. (Cables 222b and 224b are not visible in the side views of FIGS. 2A and 2B, but are visible in a perspective view of wrist 230 shown in FIG. 2C.) In the illustrated configuration, pitch joint 240 is formed by a proximal link (or proximal wrist portion) 242 and a distal link (or distal wrist portion) 244 that are mechanically connected or arranged to allow rotation about a pitch axis 246. The term "pitch" is arbitrary, and is used herein to refer to movement of the distal link 244 relative to the proximal link 242. The pitch joint 240 could alternatively employ many types of joint architectures, for example, using pins, rolling surfaces, or flexure. A pair of actuation cables 226a and 226b that attach to link 244 extend from link 244 in joint 240 through a main shaft 220 of instrument 200 to a transmission 210 of instrument 200. Each cable 222a, 222b, 224a, 224b, 226a, and 226b may include sections of stranded cable, wire, bands, ribbons, tubes, rods or similar elongated structures. In some embodiments, each cable includes sections of stranded cable crimped to hypotubes, the stranded cables being used where significant bending or winding of the cables occurs, and hypotubes being used in other sections to limit stretching of the cables. More generally, the term cable is used herein to refer to any tendon or tendon-like structure that may be pulled for actuation of a mechanism.

The transmission 210 may be configured to interface with a robot to move the cables to cause rotation of the distal link 244 relative to the proximal link 242, as well as movement of the end effector 258 relative to the distal link 244. The movement of the end effector 258, and more specifically, rotation of the jaw 252 and the jaw 254 either together or in opposition to each other (e.g., as a grip) can be performed about a yaw axis (the term yaw is arbitrary). Thus, the transmission 210 can move the proximal end of any combination of the cables by any suitable mechanism to produce the desired movement. In some embodiments, the transmission 210 (and any of the transmissions described herein) can include a capstan or other motor-driven roller that rotates or "winds" the cables to produce movement. For example, in some embodiments, the transmission 210 can include any of the backend assemblies or components described in U.S. Pat. No. 9,204,923, entitled "Medical Instrument Electronically Energized Using Drive Cables," which is incorporated herein by reference in its entirety.

For pitch actuation (i.e., rotation of the distal link 244 about the pitch axis 246), the transmission 210 may include a conventional drive mechanism (not shown, also referred to as an actuator) that is powered by a motor. In particular, a control robot may operate a conventional drive mechanism in the transmission 210 to reel in one cable 226a or 226b and pay out the other cable 226b or 226a and thereby rotate the distal link 244 relative to proximal link 242. FIG. 2A shows medical instrument 200 in a first (or unbent) configuration, and FIG. 2B shows medical instrument 200 in a second configuration in which a length of cable 226b has been let out and a length of cable 226a has been pulled in to cause the distal link 244 (and the more distal portions of medical instrument 200) to rotate relative to the proximal link 242 about the pitch axis 246.

Figure 2C:
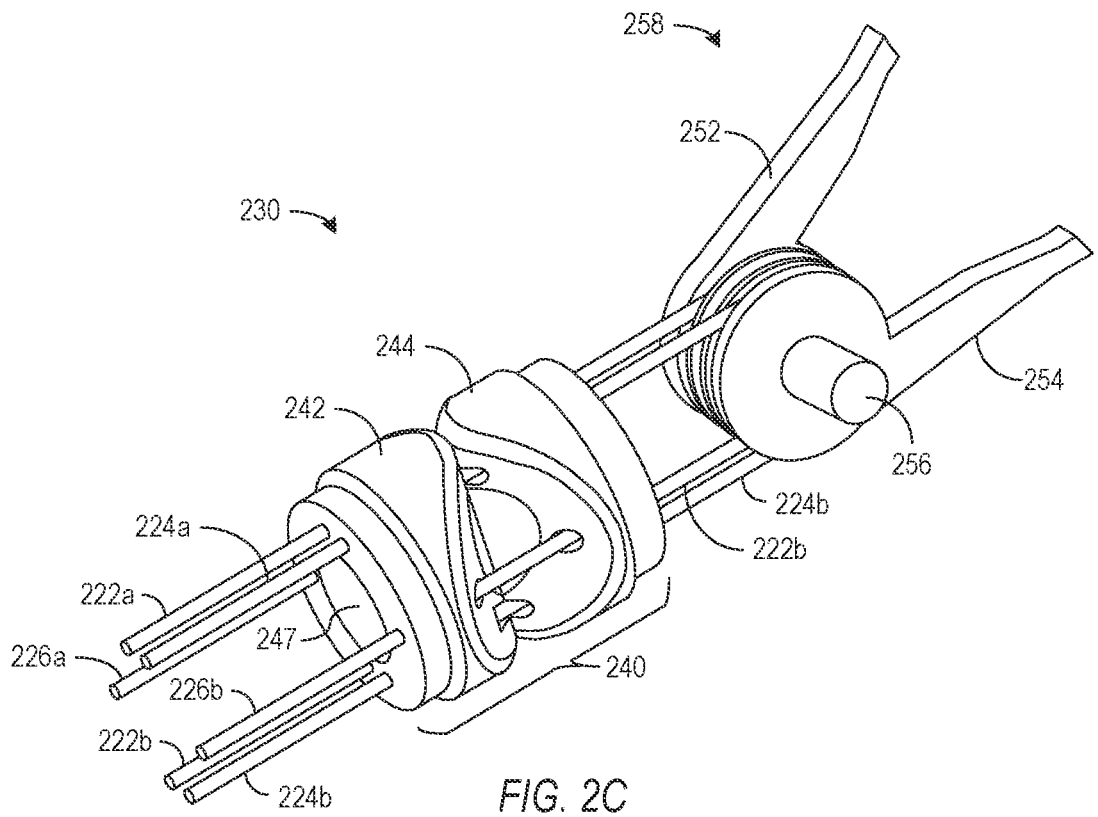
FIG. 2C shows a perspective view of a wrist that can be included in the medical instrument of FIGS. 2A and 2B.

Cables 222a and 222b, which pass through joint 240, are used to actuate the jaw 252, e.g., to rotate jaw 252 about a yaw axis corresponding to a pivot 256. Cables 224a and 224b are used to actuate the jaw 254, e.g., to rotate jaw 254 about the yaw axis corresponding to pivot 256. As shown, the joint 240 does not include cable paths that permit cables 222a, 222b, 224a, and 224b to all pass through joint 240 along cable length conserving paths. Similarly stated, the joint 240 does not define cable paths that pass through the pitch axis 246. For example, as shown in FIG. 2C, links 242 and 244 may require space for a central lumen 247 that passes through links 242 and 244 for work site irrigation, pressurization or for other medical systems such as a vision system (not shown). Cables 222a and 222b thus do not pass through the rotation axis 246 of joint 240. Rather, as shown, the cables 222a and 222b pass through pitch joint 240 at an offset to one side of the rotation axis 246 of joint 240, and cables 224a and 224b similarly pass through pitch joint 240 at an offset to the opposite side of the axis 246 of joint 240. In some embodiments, the offset distance of cables 222a and 222b from the rotation axis of joint 240 is the same as the offset distance of cables 224a and 224b from the rotation axis of joint 240.

Each pair of cables 222a and 222b or 224a and 224b may be preloaded with tension that reduces the likelihood of slack developing within the cables, and thereby keep cables 222a, 222b, 224a, and 224b engaged with guide pulleys (not shown) or with jaw 252 or 254. For example, cables 222a, 222b, 224a, and 224b may all have equal tension when the device 200 is in the first configuration shown in FIG. 2A. As shown in FIG. 2A, the wrist 230 defines a first wrist cable path 222' through which the cables 222a and 222b are routed between the distal link 244 and the proximal link 242. When the device 200 is in the first configuration, the first wrist cable path has a length $L_1$. The wrist 230 defines a second wrist cable path 224' through which the cables 224a and 224b are routed between the distal link 244 and the proximal link 242. When the device 200 is in the first configuration, the second wrist cable path has a length $L_2$. Although shown as being a symmetric implementation, in which the length $L_1$ and the length $L_2$ are equal when the device 200 is in the first configuration, in other embodiments, the length $L_1$ and the length $L_2$ may be unequal in the first (or in any other) configurations.

When joint 240 is actuated such that the distal link 244 rotates relative to the proximal link 242, as shown in FIG. 2B, the rotation of joint 240 and the offset nature of the first cable path 222' and the second cable path 224' cause the lengths of the cable paths to change (and become unequal). Specifically, in the second (or rotated) configuration, the first cable path 222' has a length $L'_1$ that is less than the length $L_1$. The reduced path length tends to reduce tension and create slack in the pair of cables 222a and 222b. Similarly, in the second (or rotated) configuration, the second cable path 224' has a length $L'_2$ that is greater than the length $L_2$. The increased path length tends to increase tension and stretch the pair of cables 224a and 224b.

To minimize cable slack or deformation of cables 222a, 222b, 224a, and 224b when the joint 240 moves, the transmission 210 includes a path length compensating drive mechanism 212 that can automatically compensate for the changes in cable path lengths in pitch joint 240. In some embodiments, the path length compensating drive mechanism 212 can change a length of a cable path within the transmission 210 (i.e., a transmission cable path) in response to a change in the length of a corresponding wrist cable path. For example, in some embodiments, the path length compensating drive mechanism 212 can change a length of a cable path within the transmission 210 through which the cable pair 222a and 222b is routed in response to the decrease in the path length indicated by $L'_1$. In this manner, the overall cable path length (from the transmission 210 and through the joint 240) remains substantially constant (i.e., the path length is conserved). In some embodiments, the path length compensating drive mechanism 212 can change a length of a cable path within the transmission 210 (i.e., a transmission cable path) in response to a change in the force exerted by the cables. For example, in some embodiments, the path length compensating drive mechanism 212 can change a length of a cable path within the transmission 210 through which the cable pair 222a and 222b is routed in response to a decrease in the tension force exerted by the cable pair 222a and 222b on the drive mechanism 212.

Figure 3:
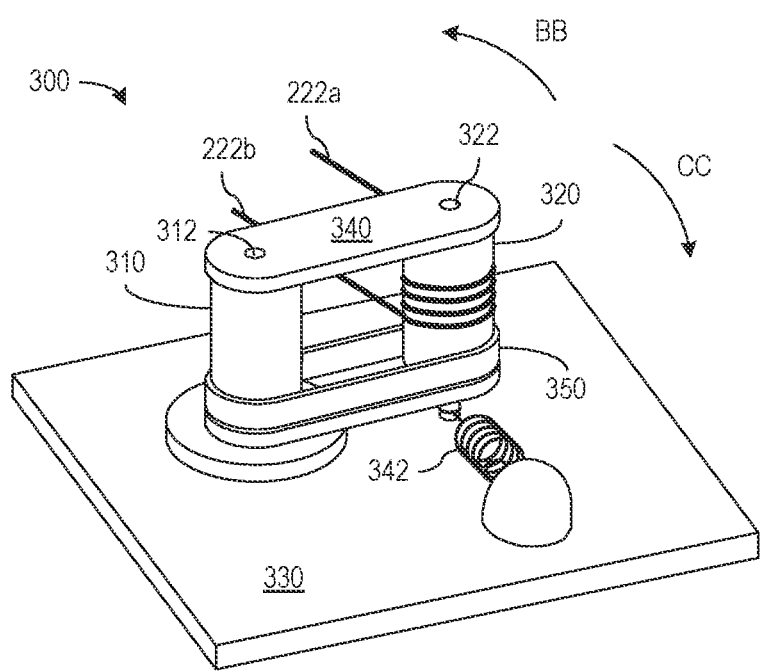
FIG. 3 shows a perspective view of a path length compensating drive mechanism for a pair of actuation cables, according to an embodiment.

In some embodiments, a transmission can include an adjustment mechanism that compensates for changes in the path length of a pair of cables within a wrist or joint assembly by moving position of an actuator within the transmission. For example, in some embodiments, a transmission (e.g., the transmission 210) can include a capstan about which a cable pair is wound, and an adjustment mechanism can change the rotation axis of the capstan to change the length of the cable path within the transmission. For example, FIG. 3 shows a drive mechanism 300 that may be used in an instrument transmission to drive a pair of cables 222a and 222b having distal routings that do not conserve cable length. Drive mechanism 300 includes an input spindle 310 that is rotatably mounted at a fixed location on a chassis 330 within the instrument transmission. The location of spindle 310 may be fixed according to the position of an external actuator, such as a drive motor (not shown) in a docking port for the medical instrument. For example, a control robot (not shown) may have a docking port that accommodates interchangeable medical instruments, and the transmission of each interchangeable medical instrument may be shaped to fit the docking port and may require one or more input spindles being fixed at locations corresponding to the drive motors in the docking port. The specifications of the docking port of the robot may thus dictate the size, shape, and location of spindle 310 on chassis 330.

The drive mechanism 300 includes at least one capstan 320 around which cables 222a and 222b are wound. The drive mechanism further includes a mounting 340 that permits movement of the capstan 320. The adjustment of the capstan position can be used to adjust a length of a cable path within the transmission. The adjustment of the capstan position can also keep the tension in cables 222a and 222b constant or in a desired working range. The capstan 320 may be a cylindrical capstan mounted on the axle 322. As shown in FIG. 3, mounting 340 includes one or more arms, and each arm is attached to rotate about a fixed axle 312 of spindle 310, and the arms holds capstan axle 322 at a fixed distance from spindle axle 312. In use, the location of capstan axle 322 can move along a circular path about spindle axle 312. Moreover, the drive mechanism 300 includes an adjustment mechanism, which includes the mounting 340 and a spring system 342. The spring system 342 biases the capstan 320 and the mounting 340 to pull or push against the tension force exerted by the cables 222a and 222b on the capstan 320. In this manner, the drive mechanism 300 (and the adjustment mechanism therein) function to maintain or limit the tension in cables 222a and 222b. In particular, the spring system may apply a force to capstan 320 that opposes the forces that cables 222a and 222b apply to capstan 320.

FIG. 3 shows a specific implementation in which spring system 342 is a spring having one end fixed on chassis 330 and another end coupled to mounting 340 or axle 322. Other embodiments, however, can include any suitable spring system configuration or biasing system to oppose the tensions in cables 222a and 222b. For example, in some embodiments, a spring may be either stretched or compressed to apply force to mounting 340 or axle 322. Also, many types of springs such as a coil spring or a flexure may be employed. The spring system may also act as a Hooks law spring, which may allow the preload tension in cables 222a and 222b to vary with the position of axle 322, or as a constant force spring that maintains a constant average tension in cables 222a and 222b. In in some embodiments, the spring system may be incorporated in the arms of mounting 340, e.g., the arms may be fixed at spindle axle 312 and may flex to provide both movement of axle 322 and spring force to oppose tension in cable 222a and 222b.

The drive mechanism 340 includes a drive coupling 350 between capstan 320 and spindle 310 that connects capstan 320 to rotate when spindle 310 rotates. Although the drive coupling 350 is shown as being a belt, in other embodiments, any suitable coupling can be used, that for any location or for a range of locations of axle 322, links rotation of spindle 310 about axle 312 to cause rotation of capstan 320 about axle 322. For example, in some embodiments, the drive coupling 350 can include cables, a chain drive, or a gear system.

As shown, the cable pair (i.e., cables 222a and 222b) are wound around capstan 320 so that rotation of capstan 320 about axle 322 pays out a length of one of the cables 222a or 222b and simultaneously reels in an equal length of the other cable 222b or 222a. In operation, if pitch movement of a wrist joint or other system along the main instrument shaft does not conserve cable length for cables 222a and 222b within the wrist joint, mounting 340, then the drive mechanism 300, without external intervention, can move capstan 320 to compensate for the change in cable length caused when the device rotates about the pitch axis (e.g., pitch axis 246). In particular, as the path length for the cable pair 222a, 222b decreases within the wrist joint, the spring 342 pulls axle 322 back (as shown by the arrow AA) to take up slack created in both cables 222a and 222b. Similarly, as the path length for the cable pair 222a, 222b increases within the wrist joint, the increased tension applied to the capstan 320 will cause the capstan 320 to move forward (as shown by the arrow BB) when tension in cables 222a and 222b would otherwise be potentially damaging. In particular, spring system 342, by compensating for path length changes within the wrist assembly, keeps tension in cables 222a and 222b constant or within a desired range, so that at any position of axle 322 and during movement of axle 322, rotation of fixed spindle 310 may cause rotation of capstan 320 for actuation of the actuated mechanism coupled to cables 222a and 222b.

In certain operations, a cable path length change caused by pitch actuation may happen simultaneously with yaw or grip actuation. The term grip actuation herein refers broadly to the opening or closing of a pair of jaws (e.g., the jaw 252 and the jaw 254), which may, for example, be used for gripping or releasing an object if the jaws act as forceps or a cautery tool, or for cutting if the jaws act as scissors. For grip actuation using two cable pairs (i.e., one pair for each jaw), one cable of each pair generally has low tension, while the other cable of the pair usually has a high tension to close or hold the grip. Using a separate spring-loaded route altering mechanism for each cable pair, the high tension in one cable may oppose the spring force trying to impart the length change compensation and may therefore undermine the function of a route altering system. Accordingly, in some embodiments an adjustment mechanism can conserve path lengths in two pairs of cables, and can balance the high gripping tension that may arise in one cable of one pair of cables against the accompanying high gripping tension in one cable of the other pair. An adjustment mechanism that conserves path lengths in two pairs of cables may particularly be used in a system having joints or distal mechanisms that cause complementary changes in path length. Wrist 230 of FIG. 2C, for example, routes one pair of cables 222a and 222b at an offset to one side of the pitch axis 246 and routes cables 224a and 224b at the same offset to an opposite side of the pitch axis 246. As a result, pitch movement increases the cable path length within the wrist for one cable pair 222a and 222b or 224a and 224b by an amount equal to the decrease in the cable path length within the wrist for the other cable pair 224a and 224b or pair 222a and 222b. A cable length conserving drive mechanism may thus include an adjustment mechanism that simultaneously causes complementary shifts in cable routings in the transmission to compensate for the more distal changes in path lengths.

Figure 4A:
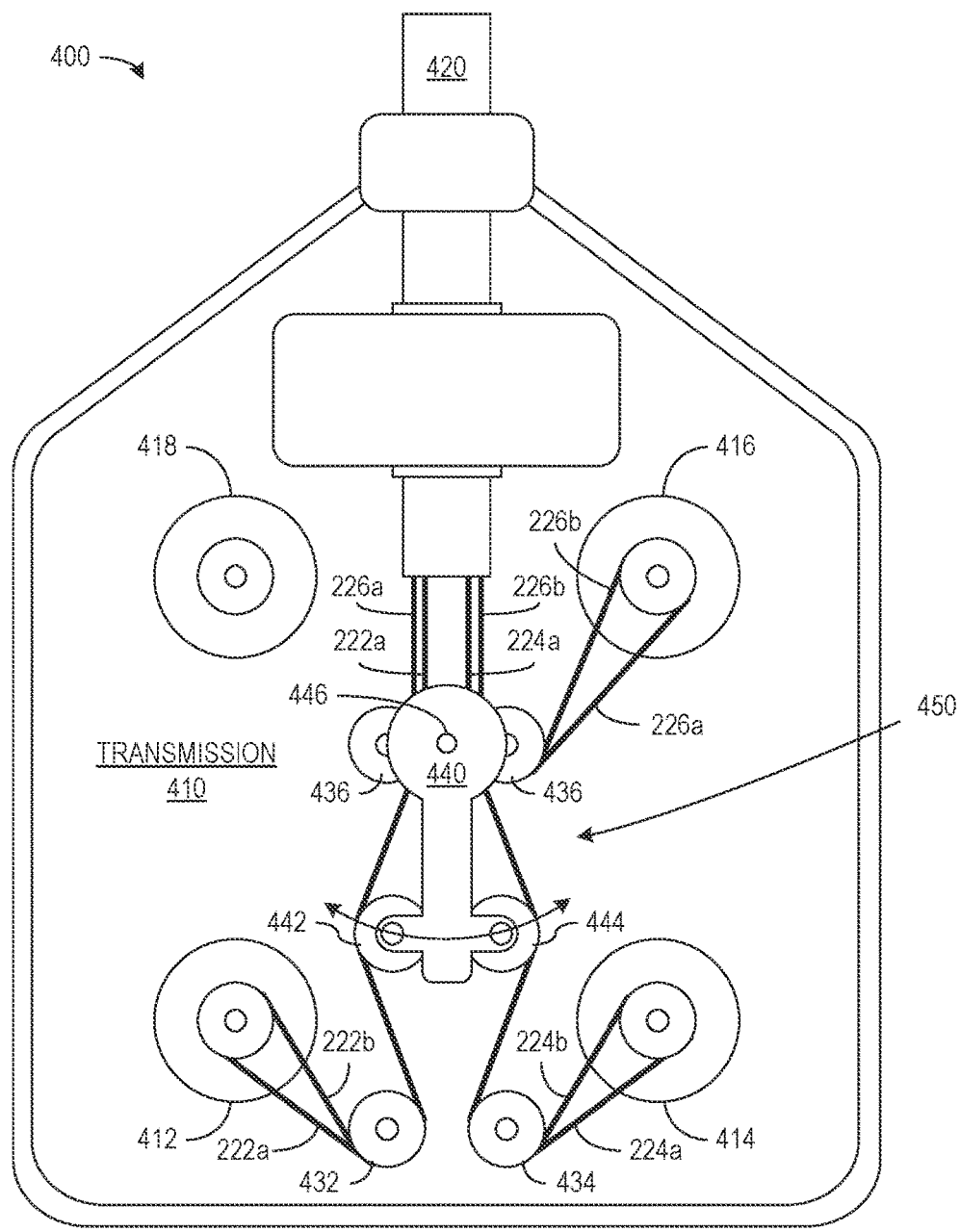
FIG. 4A shows a top view of a proximal portion of a medical instrument with a path length compensating drive mechanism, according to an embodiment.
Figure 4B:
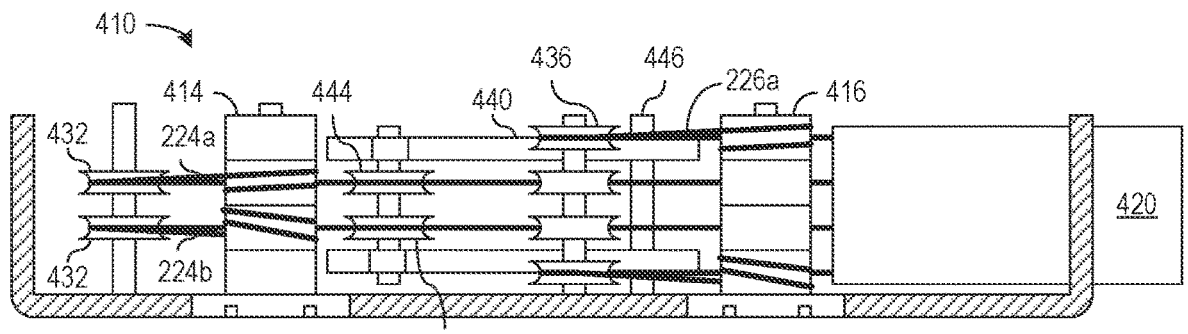
FIG. 4B shows a side view of the proximal portion of the medical instrument of FIG. 4A.

In some embodiments, for example, an adjustment mechanism can be within in a transmission of an instrument and can adjust a transmission cable path length (i.e., the length of the cable pair as routed within the transmission) for multiple cable pairs. For example, in some embodiments, an adjustment mechanism can receive input from two or more cable pairs to simultaneously increase a transmission cable path for one of the cable pairs while decreasing a transmission cable path for the other of the cable pairs. For example, in some embodiments, a medical instrument can include an adjustment mechanism having a pivot arm (or pendulum) that is within the transmission of the instrument, and that equalizes tension in opposing pairs of cables. For example, FIGS. 4A and 4B show a plan view and a cut-away side view of a portion of a medical instrument 400 having a transmission 410 from which a main instrument shaft 420 extends. The instrument includes a wrist (not shown, but which could be similar to the wrist 230 of FIG. 2C) or any other actuated mechanism that causes path length changes in a first cable pair 222a and 222b that are opposite to path length changes in a second cable pair 224a and 224b. The wrist can be coupled to the distal end of main shaft 420.

The transmission 410 includes four input spindles 412, 414, 416, and 418 that are positioned on the chassis of transmission 410, as needed to interface with actuators in a docking port of a control robot. Input spindles 412 and 414 correspond to the distal-most degrees of freedom motion of medical instrument 400, e.g., yaw movements of a pair of jaws (not shown, but similar to the jaws 252, 254). Spindle 416 corresponds to a degree of freedom of motion of a wrist joint (e.g., pitch motion), which, as described herein can cause path length changes at a location outside of the transmission 410. Specifically, actuation of the cable pair 226a and 226b by the spindle 416 can produce a change in the length of a wrist cable path for the cable pair 222a and 222b and the cable pair 224a and 224b. Spindle 418 may correspond to another degree of freedom of motion of medical instrument 400, e.g., axial rotation of main shaft 420. As described herein, the instrument 400 does not include input from an external control device, e.g., the control robot, to dynamically control cable path lengths, because path length compensation occurs autonomously within transmission 410 by the adjustment mechanism 450. Specifically, as described the adjustment mechanism 450 responds to tension changes caused when the distal portion of medical instrument 400 (e.g., the wrist assembly) fails to conserve cable lengths. The autonomous compensation allows the medical instrument 400 to conserve the overall cable-length (i.e., the full cable length from the transmission 410 to the distal-most end of the instrument) by adjusting the lengths of the transmission cable paths.

Capstans on spindles 412, 414, and 416 may be simple cylindrical capstans with circular cross-sections around which cables wrap. In some embodiments, cables 226a and 226b wrap in opposite directions about one or more capstans mounted on the axle of spindle 416. Fixed idler pulleys 436 redirect cables 226a and 226b into main shaft 420. From there, cables 226a and 226b may connect to a pitch joint, such as the type shown in FIG. 2C. Cables 222a and 222b wrap in opposite directions about one or more capstans mounted on the axle of spindle 412, and from there are routed by fixed idler pulleys 432, movable pulleys 442 on a pivot arm 440, and then fixed idler pulleys 436 that redirect cables 222a and 222b into main shaft 420. After extending from the transmission 410, cables 222a and 222b may pass through a non-cable length conserving routing, e.g., through wrist cable path that traverses a pitch joint (similar to that shown in FIGS. 2A-2C), and then connect to an actuated mechanism (e.g., jaw 252 of FIG. 2C). Similarly, cables 224a and 224b wrap in opposite directions about one or more capstans mounted on the axle of spindle 414 and from there are routed by fixed idler pulleys 434, movable pulleys 444 on pivot arm 440, and then fixed idler pulleys 436 that redirect cables 224a and 224b into main shaft 420. After extending from the transmission 410, cables 224a and 224b may pass through a non-cable length conserving routing, e.g., through wrist cable path that traverses a pitch joint (similar to that shown in FIGS. 2A-2C), and then connect to another actuated mechanism (e.g., jaw 254 of FIG. 2C).

The adjustment mechanism 450 includes a pivot arm 440 that is free to rotate about a pivot 446 fixed on the chassis of transmission 410. In use, the angular position of the pivot arm 440 may shift during pitch motions to maintain the desired tension in both cable pair 222a and 222b and cable pair 224a and 224b without needing external control to pay out or reel in cable length from a driving capstans on spindles 412 and 414. For example, if pitch motion tends to remotely (i.e., within a wrist) decrease cable path length and thereby reduce tension, in the first cable pair 222a and 222b and simultaneously tends to remotely (i.e., within a wrist) increase cable path length and thereby increase tension in second cable pair 224a and 224b, the increasing tension in cable pair 224a and 224b pushes pendulum 440 to rotate about pivot 446 and decrease cable path length of cable pair 224a and 224b within transmission 410. The rotation of pendulum 440 simultaneously increases the cable path length within transmission 410 for first cable pair 222a and 222b. Similarly, if pitch motion tends to remotely decrease cable path length and reduce tension, i.e., cause slack, in cable pair 224a and 224b and tends to remotely increase cable path length and increase tension in cable pair 222a and 222b, the increasing tension rotates pendulum 440 about pivot 446 in the opposite direction to decrease cable path length in transmission 410 for cable pair 222a and 222b and increase cable path length in transmission 410 for cable pair 224a and 224b. Instrument 400 thus has a cable length conserving drive mechanism within the transmission 410 that compensates for opposing changes in distal cable path lengths for two pairs of cables.

Figure 5:
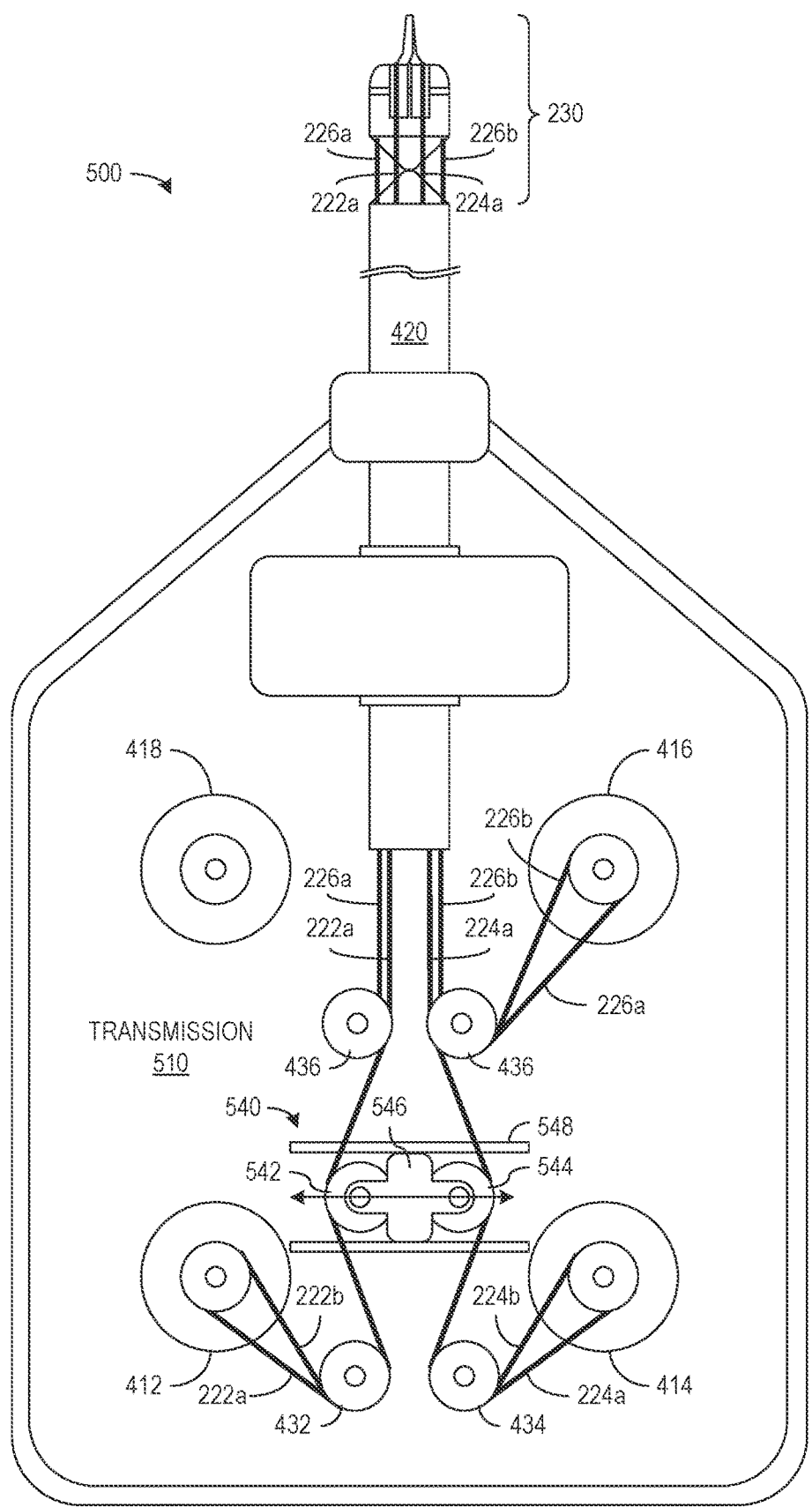
FIG. 5 shows a top view of an implementation of a medical instrument having a path length compensating drive mechanism using a sliding shuttle, according to an embodiment.

In other embodiments, a cable length conserving medical instrument can include an adjustment mechanism using a linear shuttle that shifts from side to side to change the transmission cable paths of two pairs of cables in the transmission of the medical instrument. For example, FIG. 5 shows a medical instrument 500 including a transmission 510, a main shaft 420 extending from transmission 510, and a wrist 230 at a distal end of main shaft 420. Wrist 230 can include the structures such as those described above with reference to FIGS. 2A, 2B, and 2C, and is actuated using three pairs of actuation cables as described above, e.g., cables 222a and 222b for actuation of yaw movement of one jaw, cables 224a and 224b for yaw movement of a second jaw, and cables 226a and 226b for pitch actuation of the wrist joint.

Instrument transmission 510 is similar to transmission 410 of FIGS. 4A and 4B and in particular, contains input spindles 412, 414, 416, and 418 and fixed idler pulleys 432, 434, and 436 as described above. Transmission 510 differs from transmission 410 in that transmission 510 includes an adjustment mechanism 540 that is implemented using a slide system including pulleys 542 and 544 mounted on a shuttle 546 that slides on a guide or track 548. As shown, the device 500 includes cables 222a and 222b that wrap in opposite directions about one or more capstans mounted on spindle 412. The transmission cable path for the cable pair 222a and 222b is further defined by the routing around the fixed idler pulleys 432, the movable pulleys 542 on shuttle 546, and the fixed idler pulleys 436. Cables 224a and 224b similarly wrap in opposite directions about one or more capstans mounted on spindle 414. The transmission cable path for the cable pair 224a and 224b is further defined by the routing around the fixed idler pulleys 434, the movable pulleys 544 on shuttle 546, and on fixed idler pulleys 436. During pitch movement of wrist 230, the cable path lengths of one pair of cables 222a and 222b or 224a and 224b within the wrist 230 increase while the cable path lengths of the other pair of cables 224a and 224b or 222a and 222b decrease. In response to the changes in cable path lengths in the wrist 230, and resulting change in cable tensions, the shuttle 546 slides to change the transmission cable path lengths of cables 222a, 222b, 224a, and 224b to compensate for the wrist cable path length changes in wrist 230. In this manner, the adjustment mechanism can at least approximately conserve overall cable path lengths.

Figure 6:
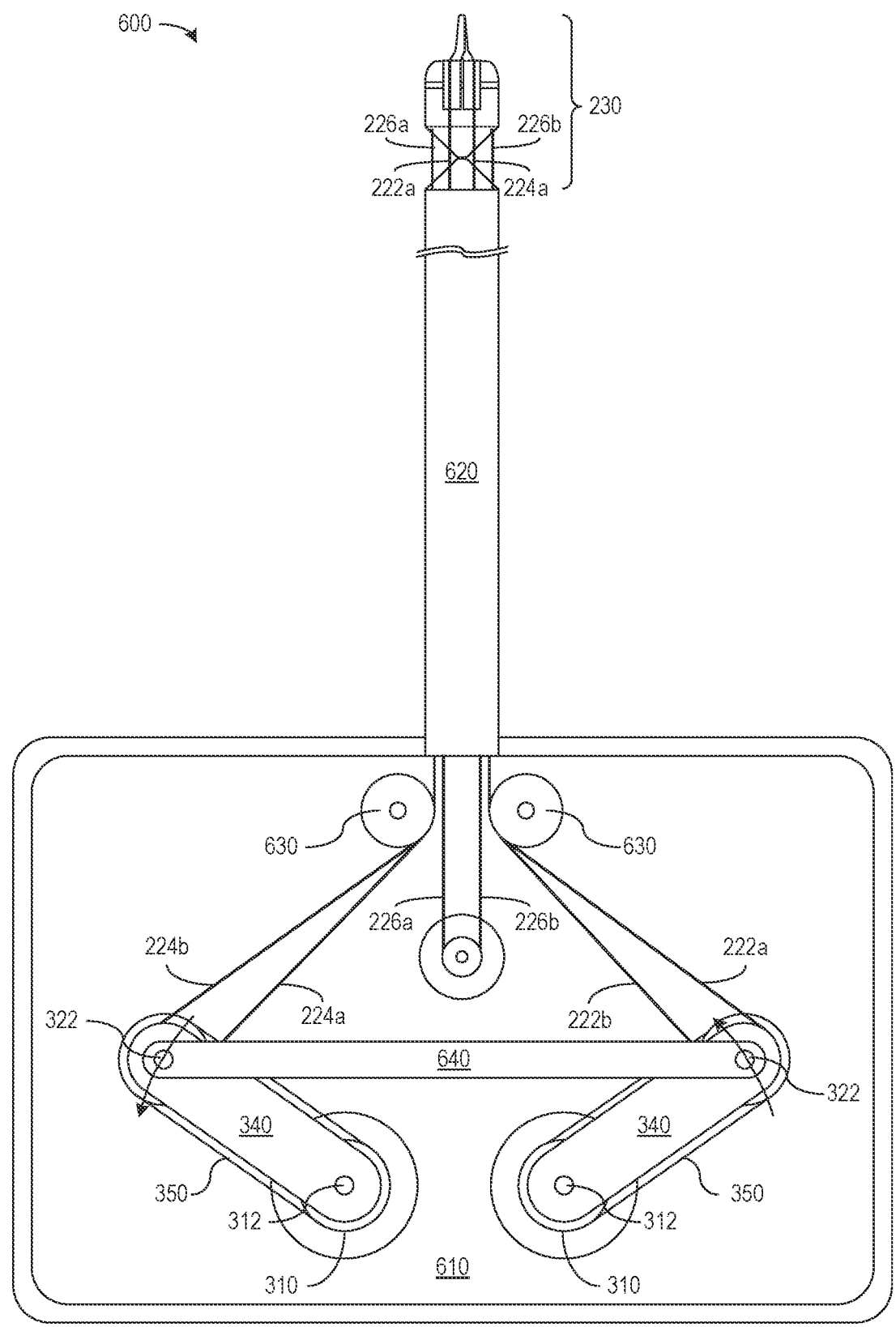
FIG. 6 shows a top view of a path length compensating drive mechanism using a bar linkage between movable capstans, according to an embodiment.
Figure 7:
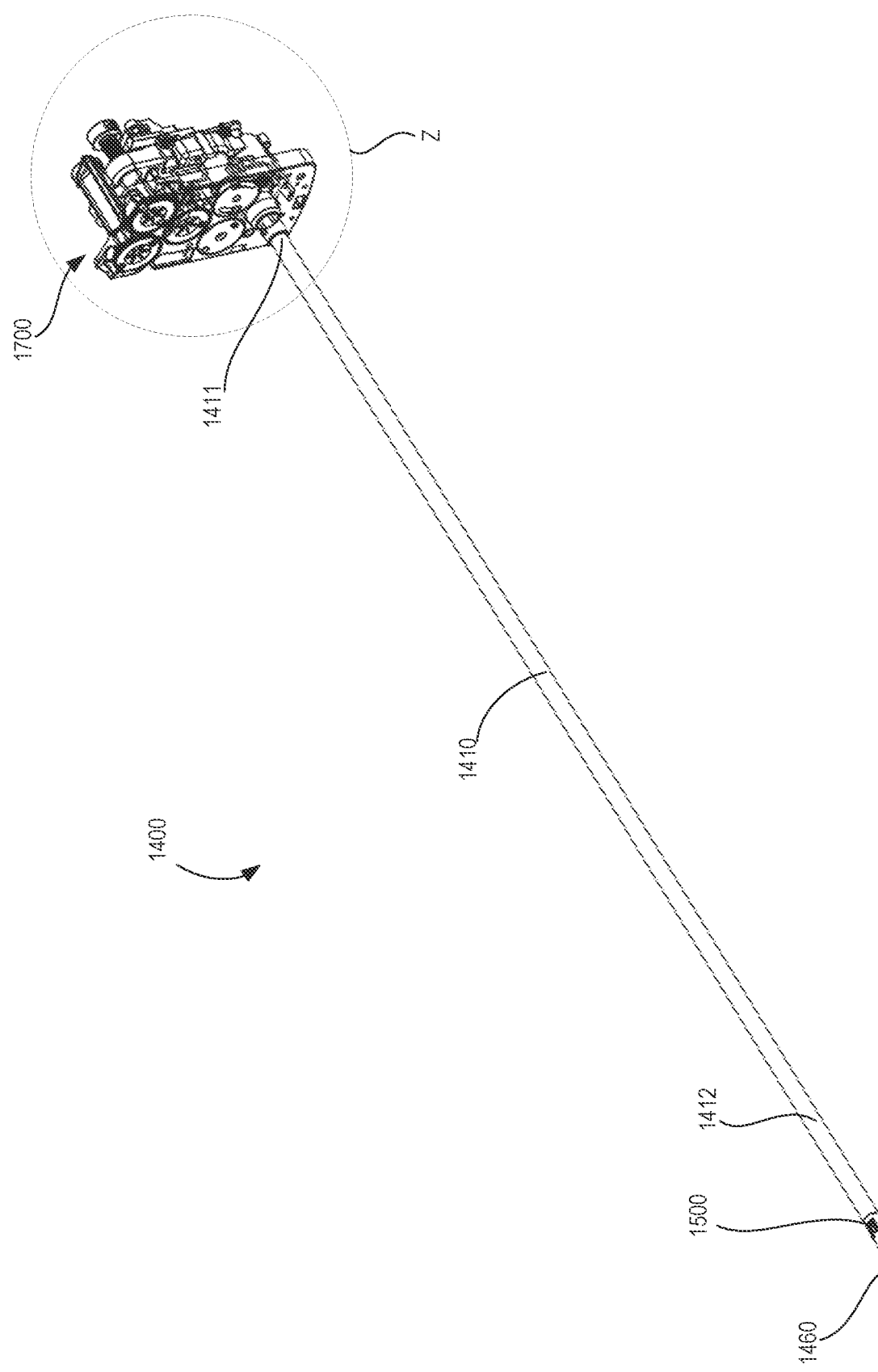
FIG. 7 is a perspective view of an instrument, according to an embodiment.

FIG. 6 shows a medical instrument 600 including a transmission 610 having another path length compensating drive mechanism that compensates for opposing path length changes in two pairs of cables for actuation of yaw degrees of freedom. In instrument 600, each pair of cables 222a and 222b or 224a and 224b used for actuation of yaw or grip rotations has a capstan 320 with a rotatable mounting 340, which can be similar to that described above with reference to FIG. 3. In particular, each capstan 320 can rotate on an axle 322, and each mounting 340 can rotate in an arc about the axle 312 of an associated drive spindle 310. Drive couplings 350 connect drive spindles 310 to respective capstans 320, so that regardless of the position of an axle 322, each capstan 320 rotates about its axle 322 in response to the associated drive spindle 310 being rotated about its axle 312.

In contrast to the system described with reference to FIG. 3, the mountings 340 in instrument 600 are not coupled to a spring system. Instead, a rigid bar 640 couples the two capstan axles 322. Mountings 340 still allow each axle 322 to rotate about the associated spindle axle 312, but link 640 connects axles 322 so that as one axle 322 rotates about its associated spindle 312, link 640 causes the other axle 322 to rotate about its associated spindle 312. Further, link 640 and mountings 340 have lengths and positions chosen so that a rotation that shortens cable path lengths of one pair of cables 222a and 222b or 224a and 224b in transmission 610 simultaneously lengthens path lengths in transmission 610 for the other pair of cables 224a and 224b or 222a and 222b. The fixed spacing of spindle axles 312 on the chassis of transmission 610, the two mountings 340, and link 630 creates a 4-bar mechanism, essentially a 4-bar pendulum, which works similarly to the pivot arm or slide systems described above. Instrument 600 may have an advantage of requiring relatively few idler pulleys 630 to route cables 222a, 222b, 224a, and 224b into main shaft 620. Cables 222a, 222b, 224a, and 224b may act as the springs in that a distal lack of cable length conservation causing increased cable tension in one cable pair and decreasing tension in the other cable pair directly and automatically actuates the route-altering mechanism to compensate for the lack of cable length conservation. Thus, the adjustment mechanism shown in FIG. 6 does not require external control.

FIGS. 7-19 are various views of an instrument 1400, according to an embodiment. In some embodiments, the instrument 1400 or any of the components therein are optionally parts of a surgical assembly that performs minimally invasive surgical procedures, and which can include a patient-side teleoperated manipulator unit, one or more kinematic linkages, one or more cannulas, or the like. The instrument 1400 includes a transmission 1700 (also referred to as a backend mechanism), a shaft 1410, a wrist assembly 1500, and an end effector 1460. The wrist assembly 1500 can be similar to any of the wrist assemblies shown and described herein. The end effector 1460 can include any suitable tool members, and can be similar to any of the end effectors described herein. The shaft 1410 can be any suitable elongated shaft that couples the wrist assembly 1500 to the transmission 1700. Specifically, the shaft 1410 includes a proximal end portion 1411 that is coupled to a housing 1760 of the transmission 1700, and a distal end portion 7412 that is coupled to the wrist assembly 1500 (e.g., a proximal link of the wrist assembly 1500, similar to the link 242 described above). The shaft 7410 defines a passageway or multiple passageways through which the cables (described below) and other components (e.g., electrical wires, ground wires, or the like) can be routed from the transmission 1700 to the wrist assembly 1500.

The instrument 1400 includes cables that couple the transmission 1700 to the wrist assembly 1500 and the end effector 1460. The instrument 1400 is configured such that movement of the cables can produce rotation of the wrist assembly 1500 about a joint axis (e.g., similar to the pitch axis 246 described above), rotation of the end effector 1460 about an axis of rotation (e.g., similar to the axis 256 described above, also referred to as the yaw axis), grip rotation of the tool members of the end effector 1460 about the yaw axis, or any combination of these movements. Changing the pitch, yaw, or grip of the instrument 1400 can be performed by manipulating the cables within the transmission 1700. Specifically, referring to FIGS. 8, 10, and 15-17, the instrument 1400 includes a first cable pair 1420 and a second cable pair 1430. The first cable pair 1420 includes a cable 1420A and a cable 1420B, and has a first end (not shown) that is coupled to and actuates a tool member of the end effector 1460 (similar to the arrangement of the cable pair 222 actuating the tool member 252, shown above). The first cable pair 1420 is routed from the end effector 1460, through the wrist assembly 1500 and the shaft 1410, such that a second end 1421 of the first cable pair 1420 is within the transmission 1700 (see FIGS. 8 and 10). In this manner, the transmission 1700 can move the second end 1421 of the first cable pair 1420 to actuate the end effector 1460. The second cable pair 1430 includes a cable 1430A and a cable 1430B, and has a first end portion (not shown) that is coupled to and actuates a tool member of the end effector 1460 (similar to the arrangement of the cable pair 224 actuating the tool member 254, shown above). The second cable pair 1430 is routed from the end effector 1460, through the wrist assembly 1500 and the shaft 1410, such that a second end 1431 of the second cable pair 1430 is within the transmission 1700 (see FIGS. 8 and 10). In this manner, the transmission 1700 can move the second end 1421 of the second cable pair 1430 to actuate the end effector 1460.

In some embodiments, the instrument 1400 can include a third cable pair (not shown) that is coupled to and actuates the wrist assembly 1500. For example, the third cable pair can be similar to the cable pair 226 described above, and can be used to move a distal link of the wrist assembly 1500 relative to a proximal link of the wrist assembly 1500 (similar to the rotation of the distal link 244 relative to the proximal link 242 shown and described above). This rotation of the wrist assembly 1500 can be referred to as pitch.

Like the wrist 230 described above, the wrist assembly 1500 can define one or more wrist cable paths through which the first end of the first cable pair 1420 and the first end of the second cable pair 1430 are routed. In some embodiments, the wrist assembly 1500 can define a first wrist cable path (similar to the first wrist cable path 222' described above) through which the first cable pair 1420 is routed, and a second wrist cable path (similar to the second wrist cable path 224' described above) through which the second cable pair 1430 is routed. Moreover, when the wrist assembly 1500 is actuated to produce pitch rotation, the lengths of the wrist cable paths can change (and become unequal). Specifically, when the distal link of the wrist assembly 1500 is rotated in a first direction, a length the first wrist cable path is reduced, which tends to reduce tension and create slack in the first cable pair 1420, and a length the second wrist cable path is increased, which tends to increase tension and potentially stretch the second cable pair 1430. Conversely, when the distal link of the wrist assembly 1500 is rotated in a second direction, the length the first wrist cable path is increased, which tends to increase tension and potentially stretch the first cable pair 1420, and the length the second wrist cable path is decreased, which tends to reduce tension and create slack in the second cable pair 1430. As described below, the transmission 1700 includes an adjustment mechanism 1800 that that automatically compensates for the changes in cable path lengths that occur in the wrist assembly 1500. In this manner, the overall cable path length (from the transmission 1700 and through the wrist assembly 1500 to the actuated end effector tool member component) remains substantially constant (i.e., the path length is conserved).

Figure 9:
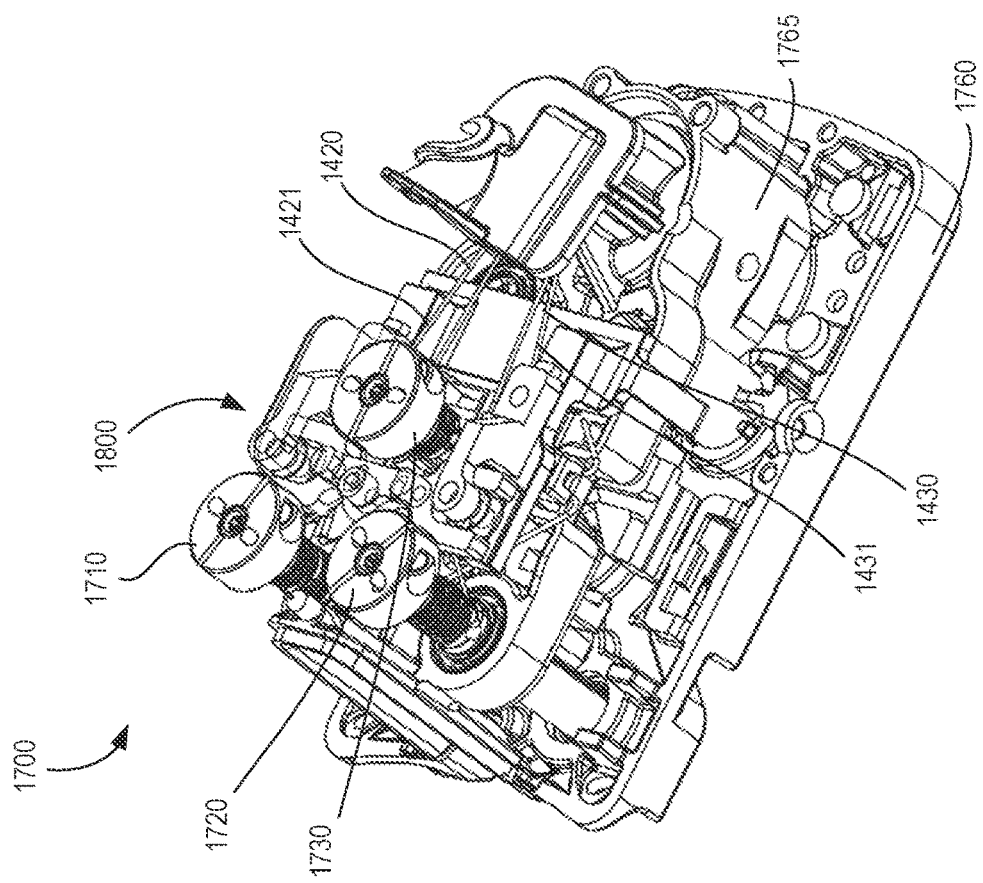
FIG. 9 is a perspective view of the transmission shown in FIG. 8.
Figure 8:
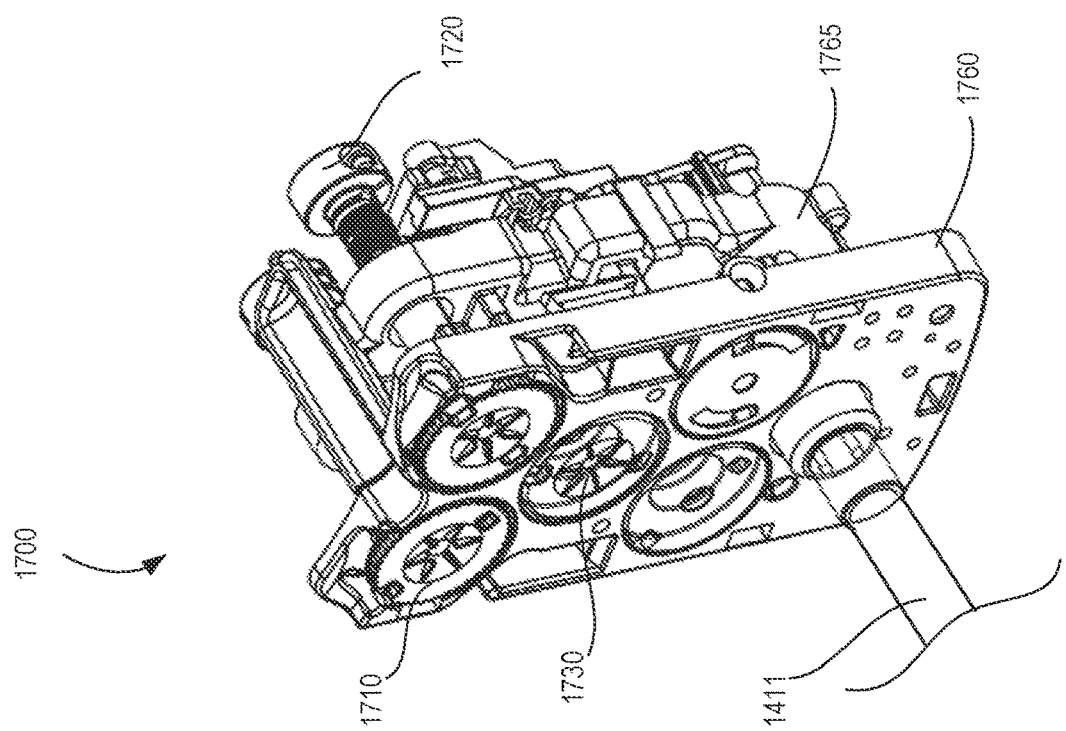
FIG. 8 is an enlarged perspective view of a transmission at the proximal end portion of the instrument indicated by the region Z shown in FIG. 7.
Figure 10:
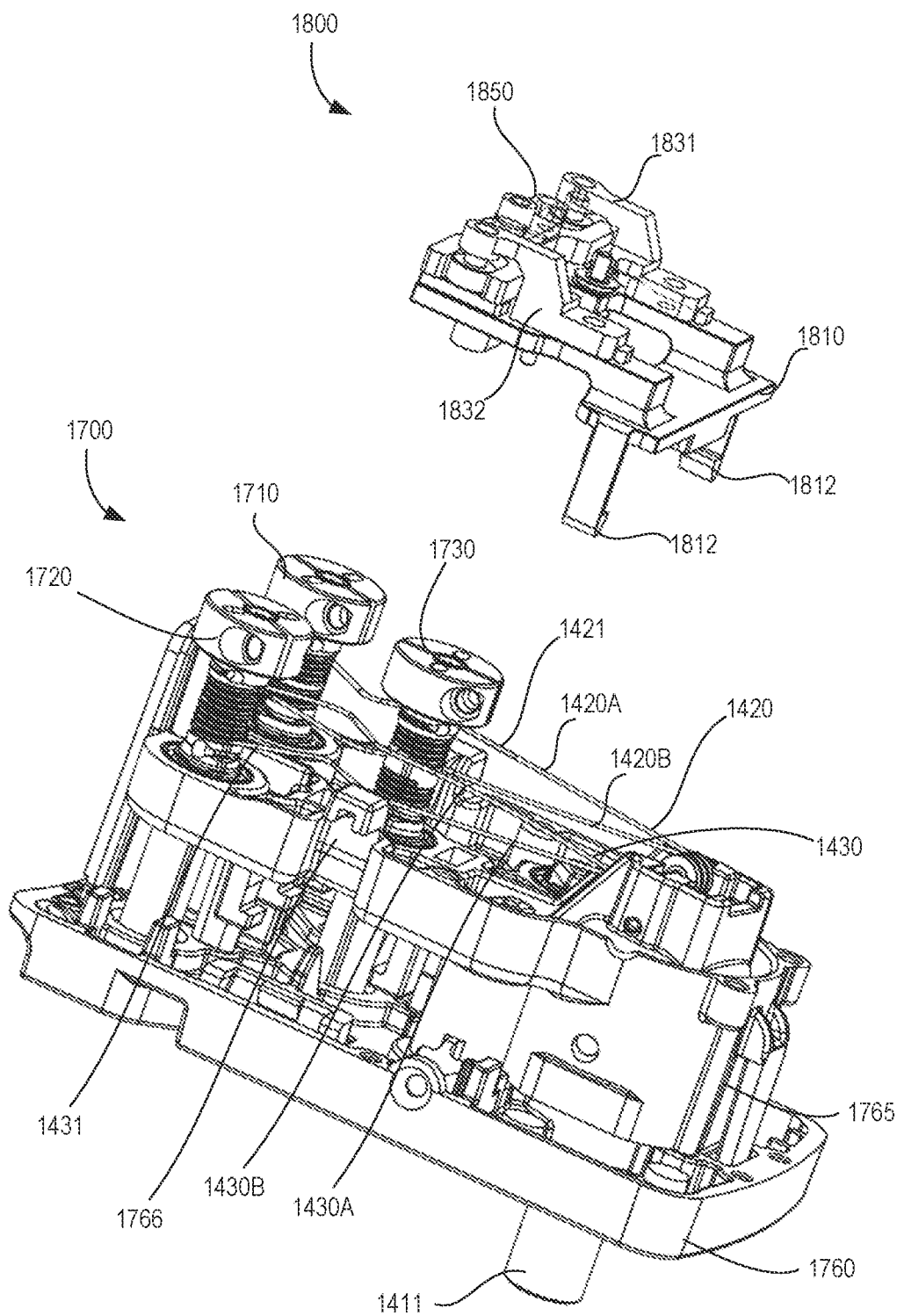
FIG. 10 is a perspective exploded view of the transmission shown in FIG. 8, showing an adjustment mechanism, according to an embodiment.

The transmission 1700 produces movement of each of the cable pairs to produce the desired movement (pitch, yaw, or grip) at the wrist assembly 1500. Specifically, the transmission 1700 includes components and controls to move some of the cables in a proximal direction (i.e., pulling or "pay in") while simultaneously allowing the distal movement (i.e., releasing or "pay out") of other of the cables. For example, proximal movement of the cable 1420A and corresponding distal movement of the cable 1420B will produce rotation of a tool member (e.g., the tool member 252) about a yaw axis. Referring to FIGS. 8-10, the transmission 1700 includes a chassis 1760, a first capstan assembly 1710, a second capstan assembly 1720, a third capstan assembly 1730, and an adjustment mechanism 1800.

The chassis 1760 provides the structural support for mounting and aligning the components of the transmission 1700. For example, the chassis 1760 defines an opening within which the proximal end portion 1411 of the shaft 1410 is mounted, and multiple openings within which the capstan assemblies are mounted. The chassis 1760 includes a mounting bracket 1765 that provides additional mounting surfaces and support (e.g., for the capstan assemblies). As shown in FIG. 10, the bracket 1765 includes a pair of mounting portions 1766 (only one of the mounting portions 1766 is shown) that engage with the mounting tabs 1812 of the cable adjustment mechanism 1800 to retain the cable adjustment mechanism 1800 within the transmission 1700. In addition to providing mounting support for the internal components of the transmission 1700, the chassis 1760 also includes external features (e.g., recesses, clips, etc.) that interface with a docking port of a drive device (not shown).

The drive device can be, for example, a computer-assisted tele-operated surgical system that can receive the instrument 1400 and manipulate the instrument 1400 to perform various surgical operations. In other embodiments, the drive device can be an assembly system that can receive and manipulate the instrument 1400 to perform various assembly operations.

The first capstan assembly 1710 includes a shaft that can be motor-driven to rotate about a capstan axle. The rotating shaft includes a portion about which the second end 1421 of the first cable pair 1420 is wrapped. In this manner, the cable 1420A extends tangentially from one side of the first capstan assembly 1710 and the cable 1420B extends tangentially from the other side of the first capstan assembly 1710. Thus, when the first capstan assembly 1710 rotates in a first direction, the cable 1420A can be moved proximally (i.e., can be pulled inward or wrapped about the rotating shaft), and the cable 1420B can be moved distally (i.e., can be payed-out or unwrapped from the rotating shaft). The movement of the cable pair 1420 can be reversed by changing the direction of rotation of the first capstan assembly 1710. The second capstan assembly 1720 includes a shaft that can be motor-driven to rotate about a capstan axle. The rotating shaft includes a portion about which the second end 1431 of the second cable pair 1430 is wrapped. In this manner, the cable 1430A extends tangentially from one side of the second capstan assembly 1720 and the cable 1430B extends tangentially from the other side of the second capstan assembly 1720. Thus, when the second capstan assembly 1730 rotates in a first direction, the cable 1430A can be moved proximally (i.e., can be pulled inward or wrapped about the rotating shaft), and the cable 1430B can be moved distally (i.e., can be payed-out or unwrapped from the rotating shaft). The movement of the second cable pair 1430 can be reversed by changing the direction of rotation of the first capstan assembly 1710.

Figure 15:
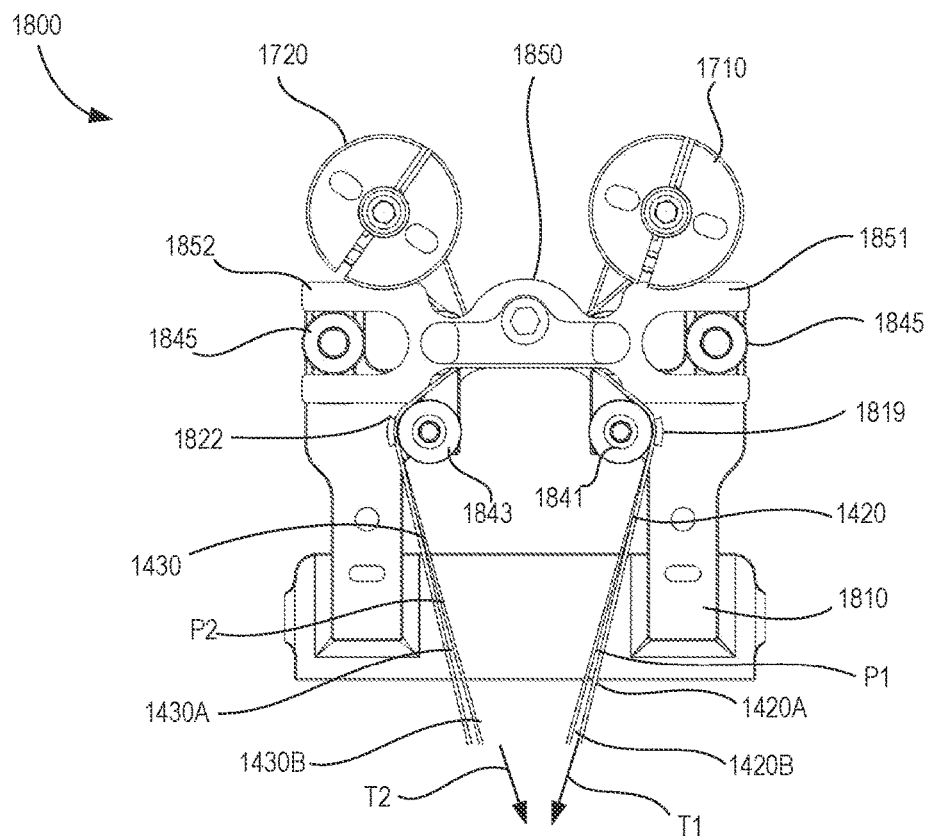
FIG. 15 is a top view of the adjustment mechanism shown in FIG. 10 in a first configuration.

Referring to FIG. 15, the arrangement of the first capstan assembly 1710 and the other components within the transmission 1700 defines a first transmission cable path P1 through which the second end 1421 of the first cable pair 1420 is routed. Similarly, the arrangement of the second capstan assembly 1720 and the other components within the transmission 1700 defines a second transmission cable path P2 through which the second end 1431 of the second cable pair 1430 is routed. As described herein, the adjustment mechanism 1800 is configured to change a length of the first transmission cable path P1 and the second transmission cable path P2 in response to change in the lengths of the corresponding wrist cable paths. In this manner, the overall cable path length (from the transmission 1700 and through the wrist assembly 1500 to the actuated end effector tool member component) for each cable pair remains substantially constant (i.e., the path length is conserved). This allows the tension within the first cable pair 1420 and the second cable pair 1430 to be maintained within the desired range regardless of the pitch position of the wrist assembly 1500.

Figure 11:
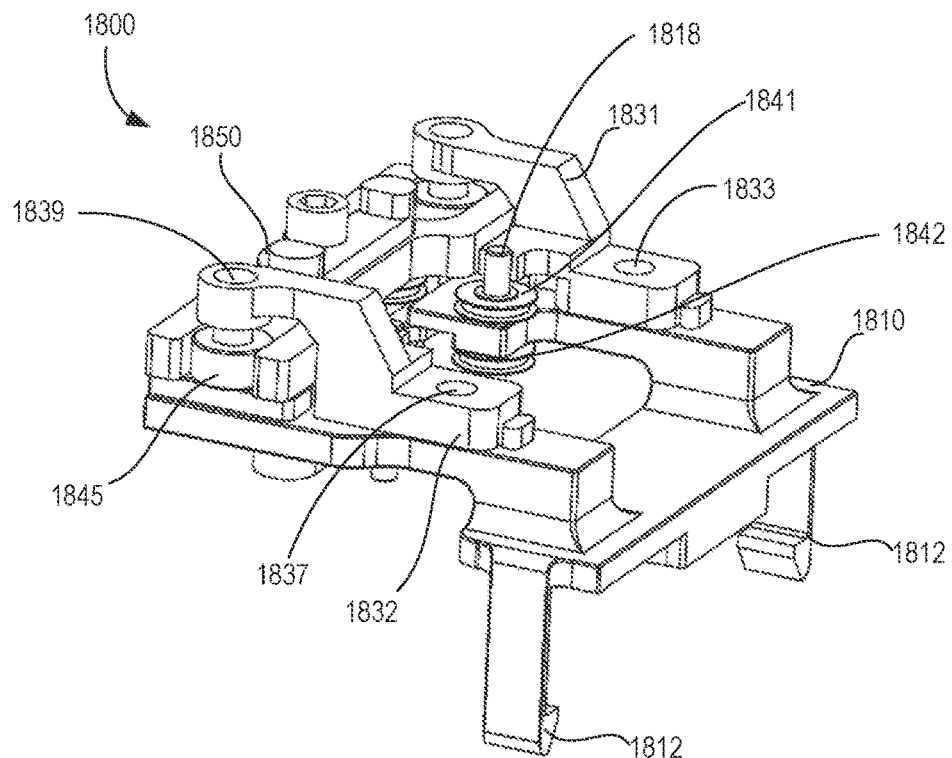
FIGS. 11 and 12 are a front perspective view (FIG. 11) and a left side perspective view (FIG. 12) of the adjustment mechanism shown in FIG. 10.
Figure 12:
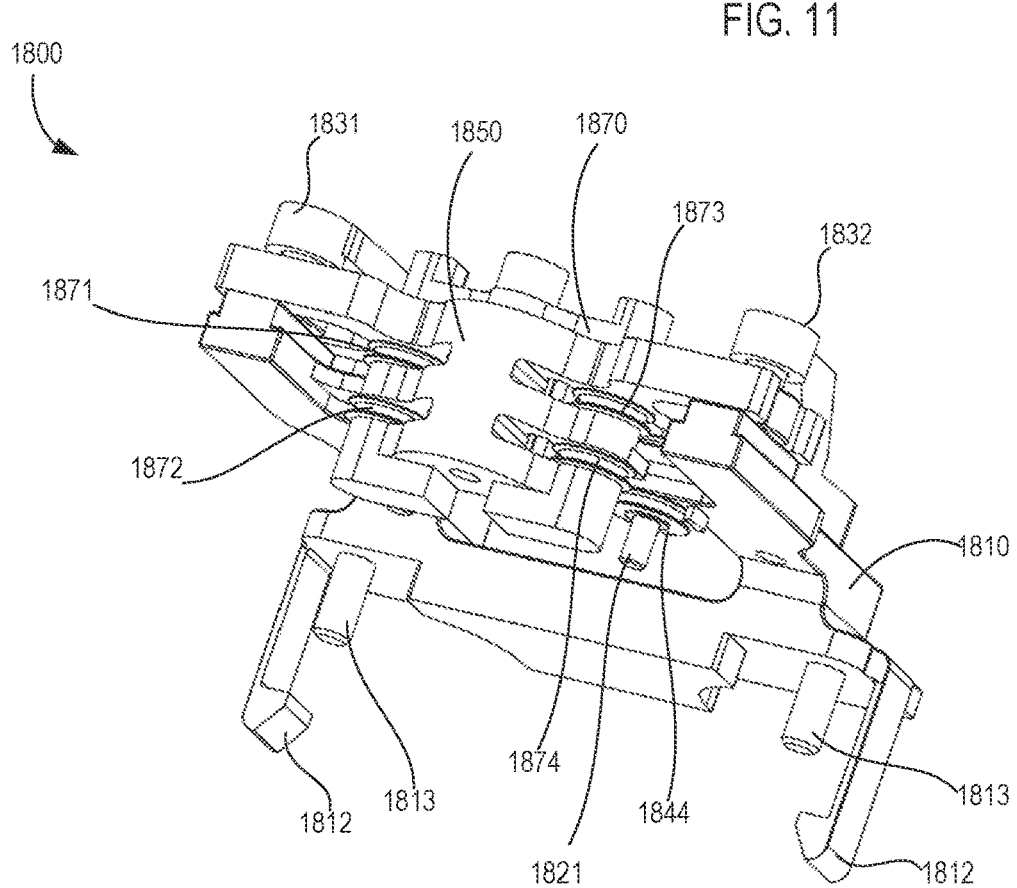
Figure 13:
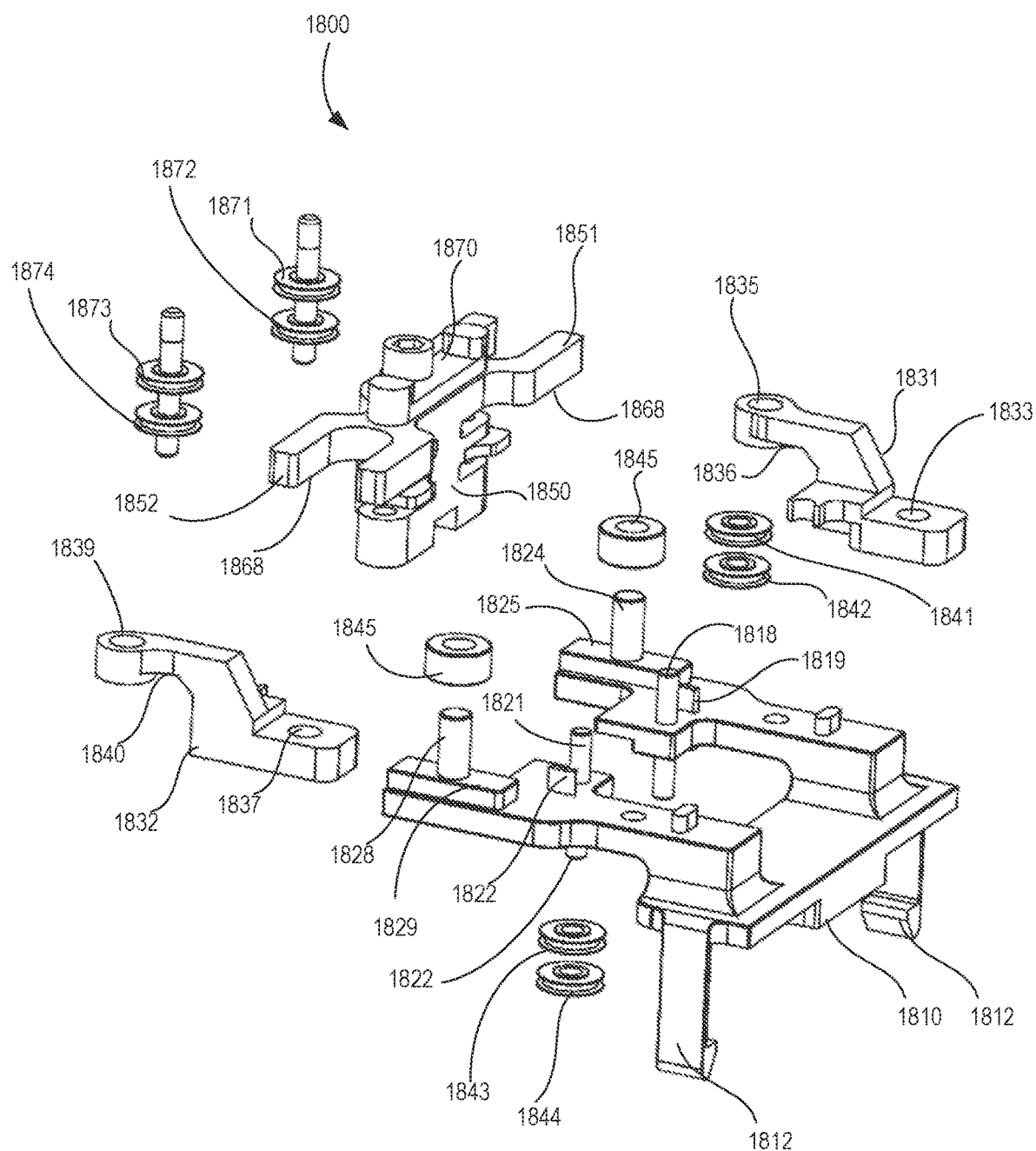
FIG. 13 is a perspective exploded view of the adjustment mechanism shown in FIG. 10.

Referring to FIGS. 11-13, the adjustment mechanism 1800 includes a frame 1810, a first mounting cap 1831, a second mounting cap 1832, and a movable member 1850. The frame 1810 is configured to be snap-fit into the chassis 1860 of the transmission 1700. Specifically, the frame 1810 includes a pair of alignment pins 1813 and a pair of connection tabs 1812 that matingly engage with the mounting bracket 1765. Referring to FIG. 10, the connection tabs 1812 are configured to be coupled to the mounting portions 1766 to retain the adjustment mechanism 1800 in place within the transmission 1700.

Referring to FIG. 13, the frame 1810 includes a first idler portion and a second idler portion. The first idler portion includes a pin 1818 and a pair of cable guides 1819. A first idler pulley 1841 is mounted to and rotates about the pin 1818 on a first (top) side of the frame 1810. The cable 1420A of the first cable pair 1420 is partially wrapped about the first idler pulley 1841. The cable guide 1819 has a curved shape that corresponds to a shape of the first idler pulley 1841, and retains the cable 1420A within the cable groove of the first idler pulley 1841. A second idler pulley 1842 is mounted to and rotates about the pin 1818 on a second (bottom) side of the frame 1810. The cable 1420B of the first cable pair 1420 is partially wrapped about the second idler pulley 1842. The cable guide 1819 on the bottom side of the frame 1810 (not shown) has a curved shape that corresponds to a shape of the second idler pulley 1842, and retains the cable 1420B within the cable groove of the second idler pulley 1842. The second idler portion includes a pin 1821 and a pair of cable guides 1822. A third idler pulley 1843 is mounted to and rotates about the pin 1821 on the top side of the frame 1810. The cable 1430A of the second cable pair 1430 is partially wrapped about the third idler pulley 1843. The cable guide 1822 has a curved shape that corresponds to a shape of the third idler pulley 1843, and retains the cable 1430A within the cable groove of the third idler pulley 1843. A fourth idler pulley 1844 is mounted to and rotates about the pin 1821 on the bottom side of the frame 1810. The cable 1430B of the second cable pair 1430 is partially wrapped about the fourth idler pulley 1844. The cable guide 1822 on the bottom side of the frame 1810 has a curved shape that corresponds to a shape of the fourth idler pulley 1844, and retains the cable 1430B within the cable groove of the fourth idler pulley 1844. By this arrangement, the idler pulleys define a portion of the first transmission cable path P1 and the second transmission cable path P2. Although the transmission cable path P1 for the first cable pair 1420 includes two slightly different paths (one for the cable 1420A and another for the cable 1420B), for simplicity, the first transmission cable path P1 is used to collectively refer to the paths for each of the cables 1420A, 1420B. Similarly, although the transmission cable path P2 for the second cable pair 1430 includes two, slightly different paths (one for the cable 1430A and another for the cable 1430B), for simplicity, the second transmission cable path P2 is used to collectively refer to the paths for each of the cables 1430A, 1430B.

The end portion of the 1810 frame includes a first pin 1824 about which a bearing 1845 is mounted and a second pin 1828 about which a bearing 1845 is mounted. A center line of the first pin 1824 and a center line of the second pin 1828 define axes of rotation for each of the bearings 1845. Moreover, as described in detail herein, the center lines of the pins 1824, 1828 define a linear path along which the movable member 1850 translates to adjust the lengths of the first transmission cable path P1 and the second transmission cable path P2. The bearings 1845 can be any suitable bearings, such as, for example, roller bearings, ball bearings, or tapered roller bearings (i.e., cone bearings). As shown in FIG. 13, the end portion of the frame 1810 also includes a pair of sliding surfaces 1825, 1829 against which corresponding surfaces 1858, 1868 can slide. The sliding surfaces 1825, 1829 can include a surface coating or treatment to reduce the friction between the frame 1810 and the movable member 1850.

The first mounting cap 1831 is coupled to the frame 1810 and secures the bearing 1845 in place, and functions to limit movement of the movable member 1850 in the upward direction. Specifically, the first mounting cap 1831 includes a first mounting hole 1833 through which a fastener can be placed to couple the first mounting cap 1831 to the frame 1810 and a second mounting hole 1835 that is coupled about the pin 1824. The first mounting cap 1831 includes a stop surface 1836 mounted above a portion of the first fork 1851 of the movable member 1850, and therefore can limit upward movement of the movable member 1850. The second mounting cap 1832 is coupled to the frame 1810 and secures the bearing 1845 in place, and functions to limit movement of the movable member 1850 in the upward direction. Specifically, the second mounting cap 1832 includes a first mounting hole 1837 through which a fastener can be placed to couple the second mounting cap 1832 to the frame 1810 and a second mounting hole 1839 that is coupled about the pin 1828. The second mounting cap 1832 includes a stop surface 1840 mounted above a portion of the second fork 1852 of the movable member 1850, and therefore can limit upward movement of the movable member 1850.

The movable member 1850 is configured to move relative to the frame 1810 to change the lengths of the first transmission cable path P1 and the second transmission cable path P2. Specifically, the movable member 1850 receives a first force from the first cable pair 1420 and a second force from the second cable pair 1430, and moves relative to the frame 1810 in response to an imbalance between the first force and the second force. As shown the movable member includes a first fork 1851, a second fork 1852, a first input portion 1861, a second input portion 1863, and a coupler 1870. The first fork 1851 includes two opposing bearing surfaces (only the bearing surface 1855 is identified) and a bottom sliding surface 1858. The movable member 1850 is coupled to the frame 1810 such that the bearing 1845 is within the opening between the opposing bearing surfaces 1855. The movable member 1850 has sufficient clearance to move in a direction normal to the sliding direction of motion, as indicated by the arrow DD in FIG. 16. In this manner, either of the opposing bearing surfaces 1855 can contact the bearing 1845 during operation of the adjustment mechanism 1800. The bottom sliding surface 1858 is in sliding contact with the corresponding sliding surface 1825 of the frame, which limits downward vertical movement of the movable member 1850 relative to the frame 1810. The second fork 1852 includes two opposing bearing surfaces (only the bearing surface 1865 is identified) and a bottom sliding surface 1868. The movable member 1850 is coupled to the frame 1810 such that the bearing 1845 is within the opening between the opposing bearing surfaces 1865. The movable member 1850 has sufficient clearance to move in a direction normal to the sliding direction of motion, as indicated by the arrow DD in FIG. 16. In this manner, either of the opposing bearing surfaces 1865 can contact the bearing 1845 during operation of the adjustment mechanism 1800. The bottom sliding surface 1868 is in sliding contact with the corresponding sliding surface 1829 of the frame, which limits downward vertical movement of the movable member 1850 relative to the frame 1810.

Figure 14:
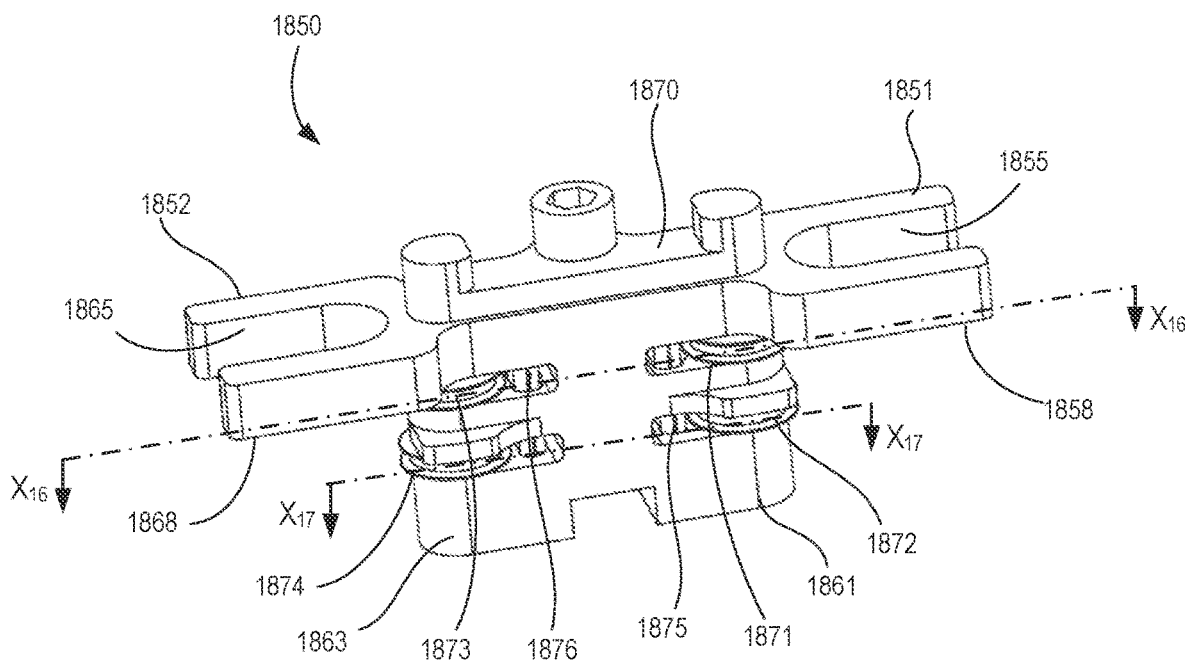
FIG. 14 is a perspective view of a movable member of the adjustment mechanism shown in FIG. 10.
Figure 16:
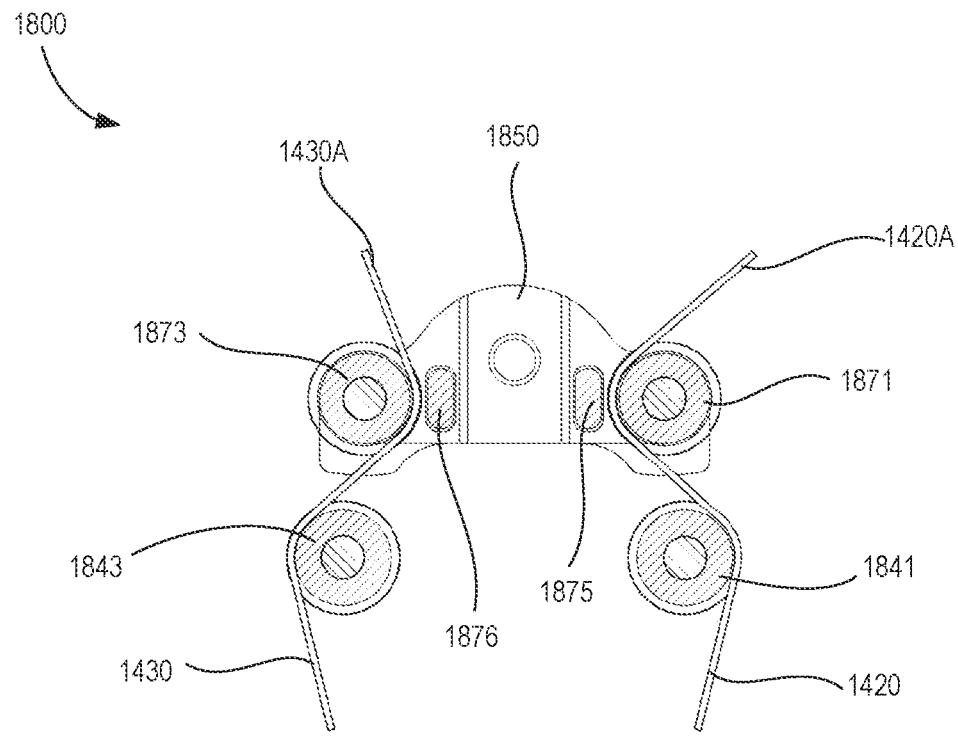
FIG. 16 is a cross-sectional view of a portion of the adjustment mechanism shown in FIG. 10 in the first configuration, the cross-section taken along line $X_{16}$-$X_{16}$ in FIG. 14.
Figure 17:
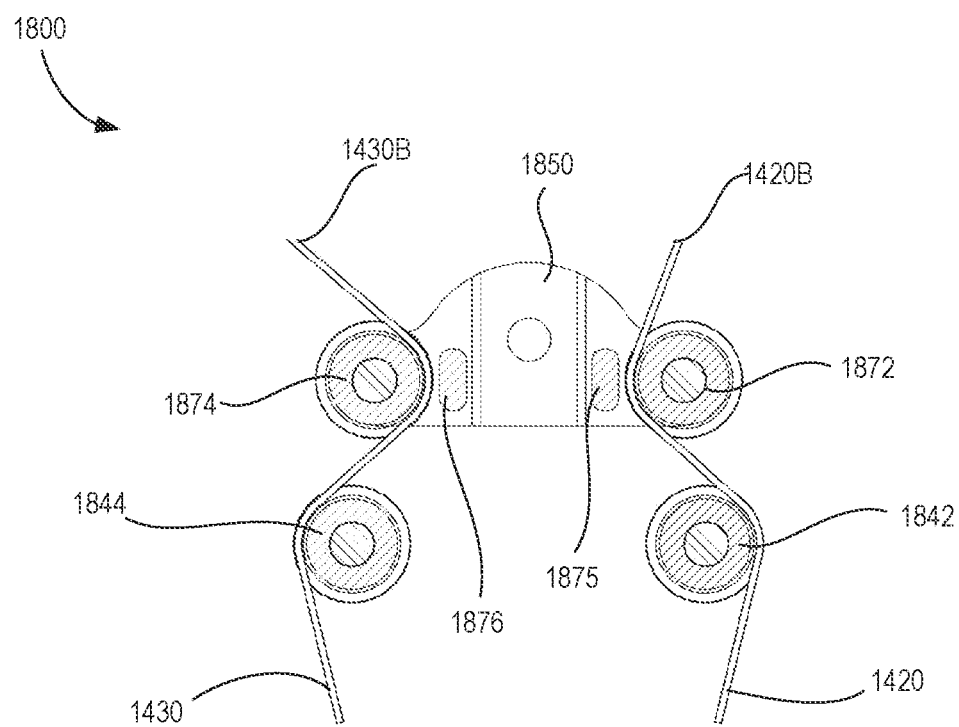
FIG. 17 is a cross-sectional view of a portion of the adjustment mechanism shown in FIG. 10 in the first configuration, the cross-section taken along line $X_{17}$-$X_{17}$ in FIG. 14.

The first input portion 1861 defines a first slot within which a first pulley 1871 is coupled and a second slot within which a second pulley 1872 is coupled. The second input portion 1863 defines a third slot within which a third pulley 1873 is coupled and a fourth slot within which a fourth pulley 1874 is coupled. The pulleys 1871, 1872, 1873, 1874 are coupled within the slots by the coupler 1870, which includes pins about which the pulleys rotate. Moreover, as shown in FIG. 14, the coupler 1870 includes a first guide pin 1875 and a second guide pin 1876. Referring to FIG. 16, the cable 1420A of the first cable pair 1420 is routed from the first idler pulley 1841 and is partially wrapped about the first pulley 1871. The first guide pin 1875 retains the cable 1420A within the cable groove of the first pulley 1871. Upon exiting the movable member 1850, the cable 1420A is routed to the first capstan assembly 1710 (see FIG. 15). Similarly, the cable 1430A of the second cable pair 1430 is routed from the third idler pulley 1843 and is partially wrapped about the third pulley 1873. The second guide pin 1876 retains the cable 1430A within the cable groove of the third pulley 1873. Upon exiting the movable member 1850, the cable 1430A is routed to the second capstan assembly 1720 (see FIG. 15).

Referring to FIG. 16, the cable 1420B of the first cable pair 1420 is routed from the second idler pulley 1842 and is partially wrapped about the second pulley 1872. The first guide pin 1875 retains the cable 1420B within the cable groove of the second pulley 1872. Upon exiting the movable member 1850, the cable 1420B is routed to the first capstan assembly 1710 (see FIG. 15). Similarly, the cable 1430B of the second cable pair 1430 is routed from the fourth idler pulley 1844 and is partially wrapped about the fourth pulley 1874. The second guide pin 1876 retains the cable 1430B within the cable groove of the fourth pulley 1874. Upon exiting the movable member 1850, the cable 1430B is routed to the second capstan assembly 1720 (see FIG. 15).

By this arrangement, the movable member 1850 (and the pulleys therein) define a portion of the first transmission cable path P1 and the second transmission cable path P2. Thus, movement of the movable member 1850 relative to the frame 1810 can adjust the lengths of the first transmission cable path P1 and the second transmission cable path P2. For example, when the instrument is the first configuration, the first cable pair 1420 has a first tension T1 and the second cable pair has a second tension T2. In some embodiments, the wrist cable paths for the first cable pair 1420 and the second cable pair 1430 have equal lengths, and thus, the tension T1 is equal to the tension T2. Under such conditions, the movable member is centered between the first pin 1824 and the second pin 1828.

Figure 18:
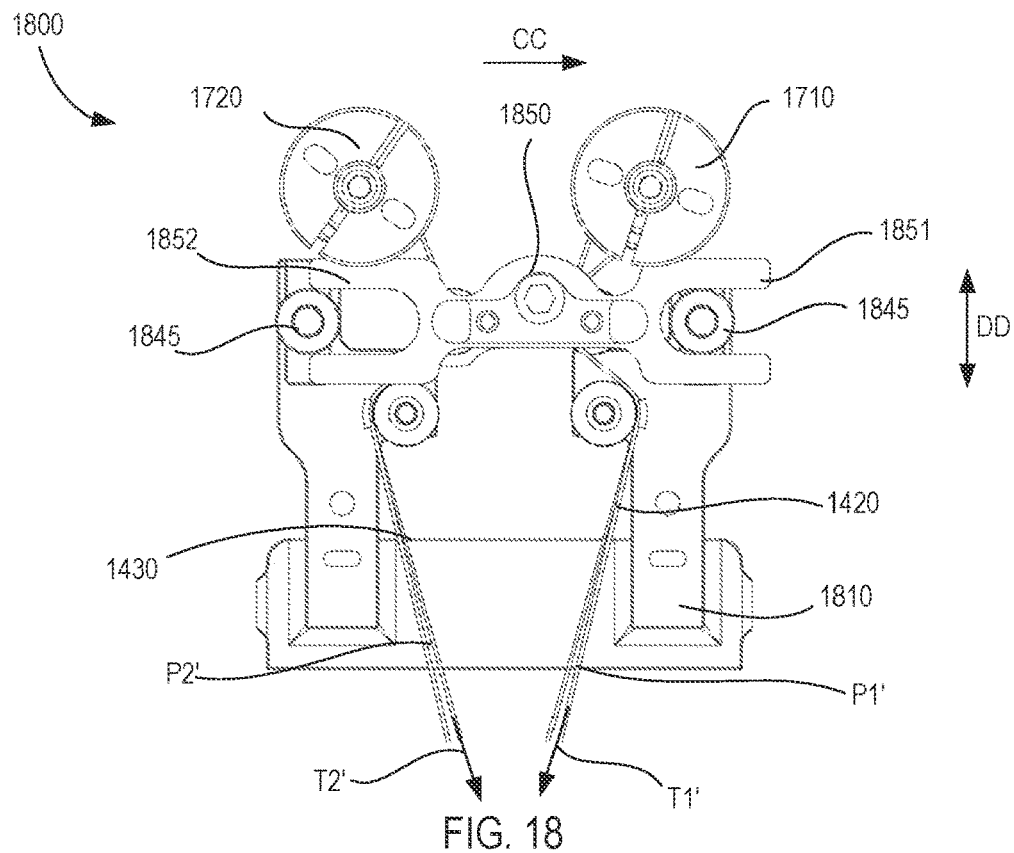
FIGS. 18-19 are top views of the adjustment mechanism shown in FIG. 10 in a second configuration (FIG. 18) and a third configuration (FIG. 19).
Figure 19:
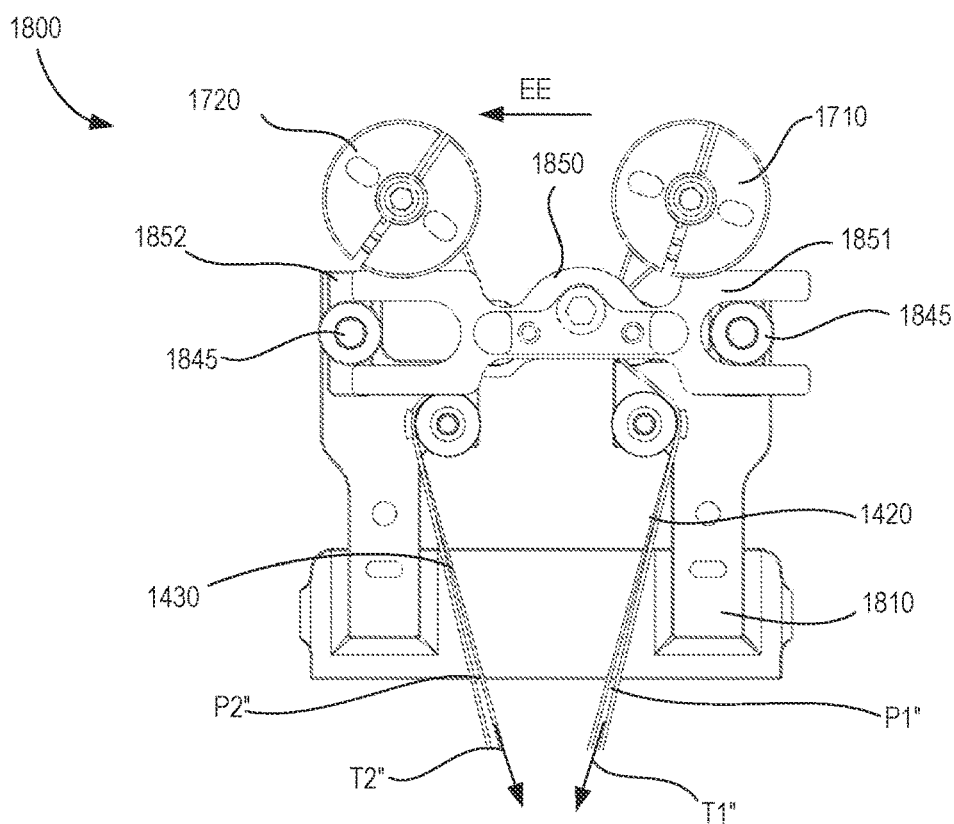

When the wrist assembly 1500 is actuated, however, the wrist cable paths can have unequal lengths, and the tension in the cable pairs can become unbalanced. For example, FIG. 18 shows a condition in which a length of the wrist cable path for the first cable pair 1420 is greater than a length of the wrist cable path for the second cable pair 1430. As described herein, this can increase the tension in the first cable pair 1420. Accordingly, when the instrument is in the second configuration, as shown in FIG. 18, the first cable pair 1420 has a first tension T1' that is greater than a second tension T2' of the second cable pair 1430. The increased tension T1' of the first cable pair 1420 acts upon the first pulley 1871 (from cable 1420A) and the third pulley 1873 (from cable 1420B). Because the tension T1' is greater than the tension T2' that acts upon the third pulley 1873 (from cable 1430A) and the fourth pulley 1874 (from cable 1430B), the movable member moves as shown by the arrow CC in FIG. 18. This movement changes the transmission cable path P1' for the first cable pair 1420 and the transmission cable path P2' for the second cable pair 1430. Specifically, the length of the transmission cable path P1' decreases and the length of the transmission cable path P2' increases. The simultaneous decrease in the transmission cable path P1' and increase in the transmission cable path P2' will stop when the tension in the first cable pair 1420 becomes equal to the tension in the second cable pair 1430. When the instrument is in the third configuration, as shown in FIG. 19, the first cable pair 1420 has a first tension T1" that is less than a second tension T2" of the second cable pair 1430. The decreased tension T1" of the first cable pair 1420 acts upon the first pulley 1871 (from cable 1420A) and the third pulley 1873 (from cable 1420B). Because the tension T1" is less than the tension T2" that acts upon the third pulley 1873 (from cable 1430A) and the fourth pulley 1874 (from cable 1430B), the movable member moves as shown by the arrow EE in FIG. 19. This movement changes the transmission cable path P1" for the first cable pair 1420 and the transmission cable path P2" for the second cable pair 1430. Specifically, the length of the transmission cable path P1" increases and the length of the transmission cable path P2" decreases. The simultaneous increase in the transmission cable path P1' and decrease in the transmission cable path P2' will stop when the tension in the first cable pair 1420 becomes equal to the tension in the second cable pair 1430. Thus, the movement of the movable member 1850 is produced by a change in the tension force in the cable pairs that results from changing cable paths within the instrument.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

Although the transmission 1700 is shown and described as including capstan assemblies used to actuate the cables, in other embodiments, any suitable actuator can be used to actuate the cables. Such actuators can include, for example, a linear actuator, an actuator that includes a gimbal-mounted component, or the like. For example, in some embodiments, a linear actuator can move each end of a cable pair by pulling (or releasing) in a linear fashion, rather than by wrapping (or unwrapping) the ends of cable pair around a capstan.

Although the first fork portion 1851 and the second fork 1852 of the movable member 1850 are shown as being symmetrical, in other embodiments, a movable member can include asymmetrical forks.

Although the adjustment mechanism 1800 is shown as being between the capstan assemblies and the exit path to the shaft 1410, in other embodiments, an adjustment mechanism can be located behind the capstan assemblies (i.e., the capstan assemblies can be between the adjustment mechanism and the exit path to the shaft 1410).

Path length compensation for two pairs of cables as described with reference to FIGS. 4A, 4B, 5, and 6 is generally not required to entirely match the change cable path length in the instrument transmission with the cable path length change in the more distal portions of the medical instrument. In particular, with pivot 440 of FIG. 4A, the changes in the path lengths for cables 222a and 222b depend on the angular position and movement of pivot 440 and the angle at which cables 222a and 222b engage movable pulleys 442. Also, the change in the cable length for cables 222a and 222b in transmission 410 may differ from the change in the cable length for cables 224a and 224b in transmission 410. A purely linear movement of moveable pulleys 542 and 544 in instrument 500 of FIG. 5 may cause slightly different changes in cable length from slightly arcing movement of pulleys 442 and 444 in instrument 400 of FIGS. 4A and 4B. The four-bar mechanism of FIG. 6 provides a response that depends on lengths of link 640, mounting arms 340, and the separation of spindle axles 312. Further, the changes in cable lengths for cables 222a, 222b, 224a, and 224b in a pitch joint or other mechanism that does not conserve cable length depend on the specific implementation of the mechanism. An exact matching of transmission path length changes to distal path length changes, however, is generally not required to keep cable tension in a safe working range.

The medical instruments and drive mechanisms as disclosed herein can provide autonomous or self-contained path length compensation or alteration, so that the medical instrument as a whole operates as a cable length conserving mechanism. In particular, drive mechanism 300 and medical instruments 400, 500, and 600 operate autonomously in that they alter, e.g., shorten or lengthen, the path lengths of one or more pairs of cables without the need for an external control system, e.g., a system that monitors cable path lengths or tensions and then actively and dynamically operates or powers a path length altering mechanism in an instrument transmission. Some disclose medical instruments may thus allow simpler control techniques and may avoid the need for additional interface components that might otherwise be required to allow an external control system to actively operate a path-length altering mechanism.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. A medical instrument comprising:
a drive mechanism;
a first capstan in the drive mechanism;
a shaft extending from the drive mechanism;
an actuated mechanism on the shaft;
a first pair of cables having a first routing in the actuated mechanism and through the shaft to the drive mechanism, the first pair of cables being wound around the first capstan, wherein an actuation of a degree of freedom of the actuated mechanism causes a change in a path length of the first pair of cables in the actuated mechanism; and
a route-altering mechanism in the drive mechanism and engaged with the first pair of cables, wherein during the actuation, the route-altering mechanism autonomously changes a path length of the first pair of cables in the drive mechanism to compensate for the change in the path length of the first pair of cables in the actuated mechanism, the route-altering mechanism including:
a first spindle fixed on a chassis of the drive mechanism,
a first mounting for the first capstan, the first mounting permitting the first capstan to rotate about an axis of the first capstan and permitting the axis of the first capstan to move relative the first spindle, and
a drive coupling connecting the first spindle to the first capstan so that rotation of the first spindle causes the first capstan to rotate.

2. The medical instrument of claim 1, further comprising:
a second pair of cables having a second routing in the actuated mechanism and through the shaft to the drive mechanism, wherein the actuation of the degree of freedom of the actuated mechanism cause a change in a path length of the second pair of cables in the actuated mechanism, wherein:
the route-altering mechanism further engages the second pair of cables to control a path length of the second pair of cables in the drive mechanism; and
during the actuation, the route-altering mechanism simultaneously increases one of and decreases another of the path length of the first pair of cables in the drive mechanism and the path length of the second pair of cables in the drive mechanism.

3. The medical instrument of claim 2, wherein the route-altering mechanism comprises:
an arm mounted to rotate about a pivot on a chassis of the drive mechanism;
a first pair of pulleys mounted on the arm and engaged with the first pair of cables; and
a second pair of pulleys mounted on the arm and engaged with the second pair of cables, wherein:
rotation of the arm in a first direction about the pivot increases the path length of the first pair of cables in the drive mechanism and decreases the path length of the second pair of cables in the drive mechanism; and
rotation of the arm in a second direction about the pivot decreases the path length of the first pair of cables in the drive mechanism and increases the path length of the second pair of cables in the drive mechanism.

4. The medical instrument of claim 2, wherein the route-altering mechanism comprises:
a shuttle mounted to slide along a guide on a chassis of the drive mechanism;
a first pair of pulleys mounted on the shuttle and engaged with the first pair of cables; and
a second pair of pulleys mounted on the shuttle and engaged with the second pair of cables, wherein:
sliding the shuttle in a first direction along the guide increases the path length of the first pair of cables in the drive mechanism and decreases the path length of the second pair of cables in the drive mechanism; and
sliding the shuttle in a second direction along the guide decreases the path length of the first pair of cables in the drive mechanism and increases the path length of the second pair of cables in the drive mechanism.

5. The medical instrument of claim 2, further comprising:
a second capstan in the drive mechanism, the second pair of cables being wound around the second capstan, wherein the route-altering mechanism comprises:
a second spindle having an axis fixed on the chassis of the drive mechanism;
a second mounting for the second capstan, the second mounting permitting the second capstan to rotate about an axis of the second capstan and permitting the axis of the second capstan to move relative the axis of the second spindle; and
a link connecting the second mounting to the first mounting so that a first movement of the axis of the first capstan causes a second movement of the axis of the second capstan.

6. The medical instrument of claim 5, further comprising:
a second drive coupling connecting the second spindle to the second capstan so that rotation of the second spindle causes the second capstan to rotate on the axis of the second capstan.

7. The medical instrument of claim 5, wherein the first movement decreases the path length of the first pair of cables in the drive mechanism and the second movement increases the path length of the second pair of cables in the drive mechanism.

8. The medical instrument of claim 1, further comprising a spring system coupled to apply a force to the axis of the first capstan that opposes forces that the first pair of cables applies.

9. The medical instrument of claim 1, wherein the first mounting limits the axis to move on an arc about the first spindle.

10. A medical instrument comprising:
a backend;
a main shaft extending from the backend;
a first pair of cables extending from the backend, through the main shaft, to an actuated mechanism, the first pair of cables being coupled to actuate a first degree of freedom of the actuated mechanism;
a second pair of cables extending from the backend, through the main shaft, to the actuated mechanism, the second pair of cables being coupled to actuate a second degree of freedom of the actuated mechanism; and
a drive mechanism in the backend and coupled to the first and second pairs of cables, the drive mechanism including a route-altering mechanism coupled to alter routings of the first and second pair of cables in response to a tension change induced by a lack of length conservation in paths of the first and second pairs of cable through the shaft to actuate the actuated mechanism, the route-altering mechanism including:
an arm mounted to rotate about a pivot on a chassis of the drive mechanism,
a first pair of pulleys mounted on the arm and engaged with the first pair of cables; and
a second pair of pulleys mounted on the arm and engaged with the second pair of cables, wherein:
rotation of the arm in a first direction about the pivot increases path lengths of the first pair of cables in the drive mechanism and decreases path lengths of the second pair of cables in the drive mechanism; and
rotation of the arm in a second direction about the pivot decreases the path lengths of the first pair of cables in the drive mechanism and increases the path lengths of the second pair of cables in the drive mechanism.

11. A medical instrument comprising:
a backend;
a main shaft extending from the backend;
a first pair of cables extending from the backend, through the main shaft, to an actuated mechanism, the first pair of cables being coupled to actuate a first degree of freedom of the actuated mechanism;
a second pair of cables extending from the backend, through the main shaft, to the actuated mechanism, the second pair of cables being coupled to actuate a second degree of freedom of the actuated mechanism; and
a drive mechanism in the backend and coupled to the first and second pairs of cables, the drive mechanism including a route-altering mechanism coupled to alter routings of the first and second pair of cables in response to a tension change induced by a lack of length conservation in paths of the first and second pairs of cables through the shaft to actuate the actuated mechanism, the route-altering mechanism including:
a shuttle mounted to slide along a guide on a chassis of the drive mechanism,
a first pair of pulleys mounted on the shuttle and engaged with the first pair of cables, and
a second pair of pulleys mounted on the shuttle and engaged with the second pair of cables, wherein:
the tension change sliding the shuttle in a first direction along the guide increases path lengths of the first pair of cables in the drive mechanism and decreases path lengths of the second pair of cables in the drive mechanism, and
the tension change sliding the shuttle in a second direction along the guide decreases the path lengths of the first pair of cables in the drive mechanism and increases the path lengths of the second pair of cables in the drive mechanism.

12. A medical instrument comprising:
a backend;
a main shaft extending from the backend;
a first pair of cables extending from the backend, through the main shaft, to an actuated mechanism, the first pair of cables be coupled to actuate a first degree of freedom of the actuated mechanism;
a second pair of cables extending from the backend, through the main shaft, to the actuated mechanism, the second pair of cables be coupled to actuate a second degree of freedom of the actuated mechanism; and
a drive mechanism in the backend and coupled to the first and second pairs of cables, the drive mechanism including a route-altering mechanism coupled to alter routings of the first and second pair of cables in response to a tension change induced by a lack of length conservation in paths of the first and second pairs of cable through the shaft to actuate the actuated mechanism, the route-altering mechanism including:
a first spindle having an axis fixed on a chassis of the drive mechanism,
a first capstan with a first mounting that permits the first capstan to rotate about an axis of the first capstan and permits the axis of the first capstan to move relative the axis of the first spindle,
a second spindle having an axis fixed on the chassis of the drive mechanism,
a second capstan having a second mounting that permits the second capstan to rotate about an axis of the second capstan and permits the axis of the second capstan to move relative the axis of the second spindle, and
a link connecting the second mounting to the first mounting so that a first movement of the axis of the first capstan causes a second movement of the axis of the second capstan.

13. The medical instrument of claim 12, further comprising:
a first drive coupling connecting the first spindle to the first capstan so that rotation of the first spindle causes the first capstan to rotate on the axis of the first capstan; and
a second drive coupling connecting the second spindle to the second capstan so that rotation of the second spindle causes the second capstan to rotate on the axis of the second capstan.

14. The medical instrument of claim 12, wherein the first movement decreases path lengths of the first pair of cables in the drive mechanism and the second movement increases path lengths of the second pair of cables in the drive mechanism.

* * * * *